(12) United States Patent
Hird et al.

(10) Patent No.: US 10,889,594 B2
(45) Date of Patent: *Jan. 12, 2021

(54) MCL-1 INHIBITORS AND METHODS OF USE THEREOF

(71) Applicant: AstraZeneca AB, Sodertalje (SE)

(72) Inventors: Alexander Hird, Waltham, MA (US); Wenzhan Yang, Waltham, MA (US); Daniel Robbins, Waltham, MA (US); Steven Kazmirski, Waltham, MA (US); Dedong Wu, Waltham, MA (US); Bo Peng, Waltham, MA (US); Jeffrey Johannes, Waltham, MA (US); Michelle Lamb, Waltham, MA (US); Qing Ye, Waltham, MA (US); Xiaolan Zheng, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/223,538

(22) Filed: Dec. 18, 2018

(65) Prior Publication Data

US 2019/0185485 A1 Jun. 20, 2019

Related U.S. Application Data

(63) Continuation of application No. 15/790,660, filed on Oct. 23, 2017, now Pat. No. 10,196,404, which is a continuation of application No. 15/493,210, filed on Apr. 21, 2017, now Pat. No. 9,840,518.

(60) Provisional application No. 62/326,156, filed on Apr. 22, 2016.

(51) Int. Cl.
  *C07D 497/22* (2006.01)
  *C07D 515/22* (2006.01)
(52) U.S. Cl.
  CPC ......... *C07D 497/22* (2013.01); *C07D 515/22* (2013.01)
(58) Field of Classification Search
  None
  See application file for complete search history.

(56) References Cited

U.S. PATENT DOCUMENTS

| 8,674,115 B2 | 3/2014 | Mermerian |
| 9,840,518 B2 | 12/2017 | Hird et al. |
| 2016/0106731 A1 | 4/2016 | Lee et al. |

FOREIGN PATENT DOCUMENTS

| WO | 2008130970 A1 | 10/2008 |
| WO | 2008131000 A2 | 10/2008 |
| WO | 2014047427 A2 | 3/2014 |
| WO | 2015031608 A1 | 3/2015 |
| WO | 2015148854 A1 | 10/2015 |

OTHER PUBLICATIONS

Alexander W. Hird, et al., A potent and selective macrocyclic inhibitor of Mcl-1 for treatment of hematologic cancers. vol. 77, Issue 13 Supplement, Cancer Research, Jul. 2, 2017, page pp. DDT01-02.
Belmonte, M. A. et al. Evaluation of Mcl-1 Inhibitors in Preclinical Models of Multiple Myeloma [abstract]. Blood 124, 652-Abstract 3428 (2014), p. 1.
Belamonte, Matthew, et al. "Development of in vitro and in vivo models to evaluate the mechanism and activity of Mcl-1 inhibitors." Gordon Research Conference, Jun. 8-13, West Dover, Vermont, p. 1.
Belmonte, Matthew, et al., "Evaluation of Mcl-1 Inhibitors in Preclinical Models of Multiple Myeloma", American Society of Hematology Annual Meeting, Washington, D.C., poster, 2014, p. 1.
Friberg, Anders, et al., "Discovery of Potent Myeloid Cell Leukemia 1 (Mcl-1) Inhibitors Using Fragment-Based Methods and Structure-Based Design", Journal of Medicinal Chemistry, 2013, 56, pp. 15-30.
Hird, Andrew W., et al., "AZD5991: A potent and selective macrocyclic inhibitor of Mcl-1 for treatment of hematological cancers", Apr. 2, 2017, AACR Annual Meeting, Washington, D.C., pp. 1-20.

(Continued)

*Primary Examiner* — Kamal A Saeed

(57) ABSTRACT

Disclosed is a compound which is 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Formula I)

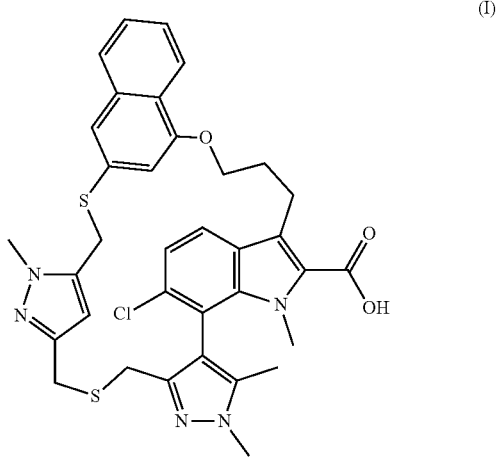

(I)

and enantiomers and pharmaceutically acceptable salts thereof. Also disclosed are pharmaceutical compositions of 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, and enantiomers and pharmaceutically acceptable salts thereof, and methods of treating cancer with such compounds and compositions.

10 Claims, 16 Drawing Sheets

Specification includes a Sequence Listing.

(56) References Cited

OTHER PUBLICATIONS

International Search Report of PCT/EP2017/059511 filed Apr. 21, 2017; Search Report dated Jun. 16, 2017, pp. 1-4.
Milan Bruncko et al: "Structure-Guided Design of a Series of MCL-1 Inhibitors with High Affinity and Selectivity", Journal of Medicinal Chemistry, vol. 58, No. 5, 2015, pp. 2180-2194.
Petros, Andrew M., et al., "Fragment-based discovery of potent inhibitors of the anti-apoptotic MCL-1 protein", Bioorganic & Medicinal Chemistry Letters 24 (2014) 1484-1488.
Tanaka, Yuta, et al., "Discovery of Potent Mcl-1/Bcl-xL Dual Inhibitors by Using a Hybridization Strategy Based on Structural Analysis of Target Proteins", Journal of Medicinal Chemistry, 2013, 56, pp. 9635-9645.

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: HyLite Fluor 647-labeled BIM peptide
<220> FEATURE:
<221> NAME/KEY: MISC_FEATURE
<222> LOCATION: (1)..(1)
<223> OTHER INFORMATION: Hilyte647 C2 Maleimide

<400> SEQUENCE: 1

Cys Trp Ile Ala Gln Glu Leu Arg Arg Ile Gly Asp Glu Phe Asn
1               5                   10                  15
```

MCL-1 INHIBITORS AND METHODS OF USE THEREOF

This application is a continuation of U.S. patent application Ser. No. 15/790,660 filed Oct. 23, 2017 which is a continuation of U.S. patent application Ser. No. 15/493,210 filed Apr. 21, 2017, now U.S. Pat. No. 9,840,518 granted Dec. 12, 2017, which claims the benefit of priority under 35 U.S.C. 119(a) to U.S. Provisional Patent Application No. 62/326,156 filed on Apr. 22, 2016. The contents of the foregoing applications are hereby incorporated by reference in their entirety.

BACKGROUND

Myeloid Cell Leukemia 1 (Mcl-1) is an important anti-apoptotic member of the BCL-2 family of proteins and a master regulator of cell survival. Amplification of the MCL1 gene and/or overexpression of the Mcl-1 protein has been observed in multiple cancer types and is commonly implicated in tumor development. In fact, MCL1 is one of the most frequently amplified genes in human cancer. In many malignancies, Mcl-1 is a critical survival factor and it has been shown to mediate drug resistance to a variety of anti-cancer agents.

Mcl-1 promotes cell survival by binding to pro-apoptotic proteins like Bim, Noxa, Bak, and Bax and neutralizing their death-inducing activities. Inhibition of Mcl-1 thereby releases these pro-apoptotic proteins, often leading to the induction of apoptosis in tumor cells dependent on Mcl-1 for survival. Therapeutically targeting Mcl-1 alone or in combination with other therapies, therefore, is a promising strategy to treat a multitude of malignancies and to overcome drug resistance in many human cancers.

SUMMARY

In one embodiment, disclosed is 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Formula I)

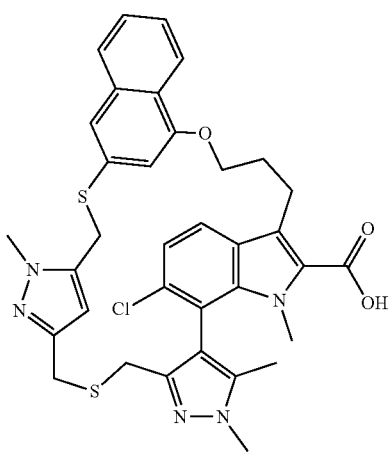

(I)

In one embodiment, disclosed is $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Formula II)

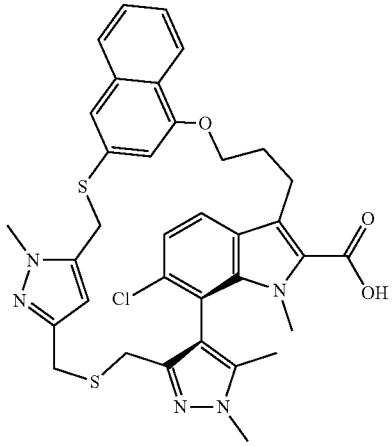

(II)

or a pharmaceutically acceptable salt thereof.

In one embodiment, disclosed is a compound which is $(S_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Formula III)

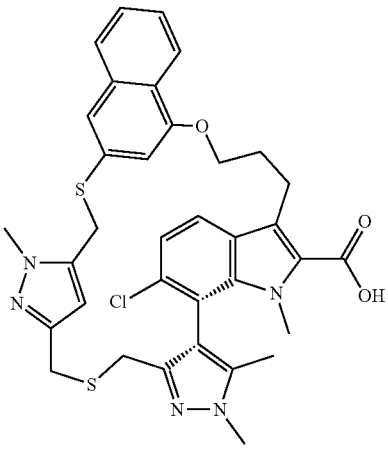

(III)

or a pharmaceutically acceptable salt thereof.

In one embodiment, disclosed is a solid form of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Formula II), or a pharmaceutically acceptable salt thereof.

In one embodiment, disclosed is a pharmaceutical composition comprising a compound of Formula (I), (II) or (III), or a pharmaceutically acceptable salt thereof and a pharmaceutical excipient, carrier or diluent.

In one embodiment, disclosed is a method of treating cancer comprising administering to a subject in need thereof a compound of Formula (I), (II) or (III), or a pharmaceutically acceptable salt thereof.

In one embodiment, disclosed is a compound of Formula (I), (II) or (III), or a pharmaceutically acceptable salt thereof, for use in treating cancer.

In one embodiment, disclosed is the use of a compound of Formula (I), (II) or (III), or a pharmaceutically acceptable salt thereof, in the manufacture of a medicament for treating cancer.

In one embodiment, disclosed is a pharmaceutical composition comprising a compound of Formula (I), (II) or (III), or a pharmaceutically acceptable salt thereof, for use in treating cancer.

DETAILED DESCRIPTION

Compounds

Figure 1:
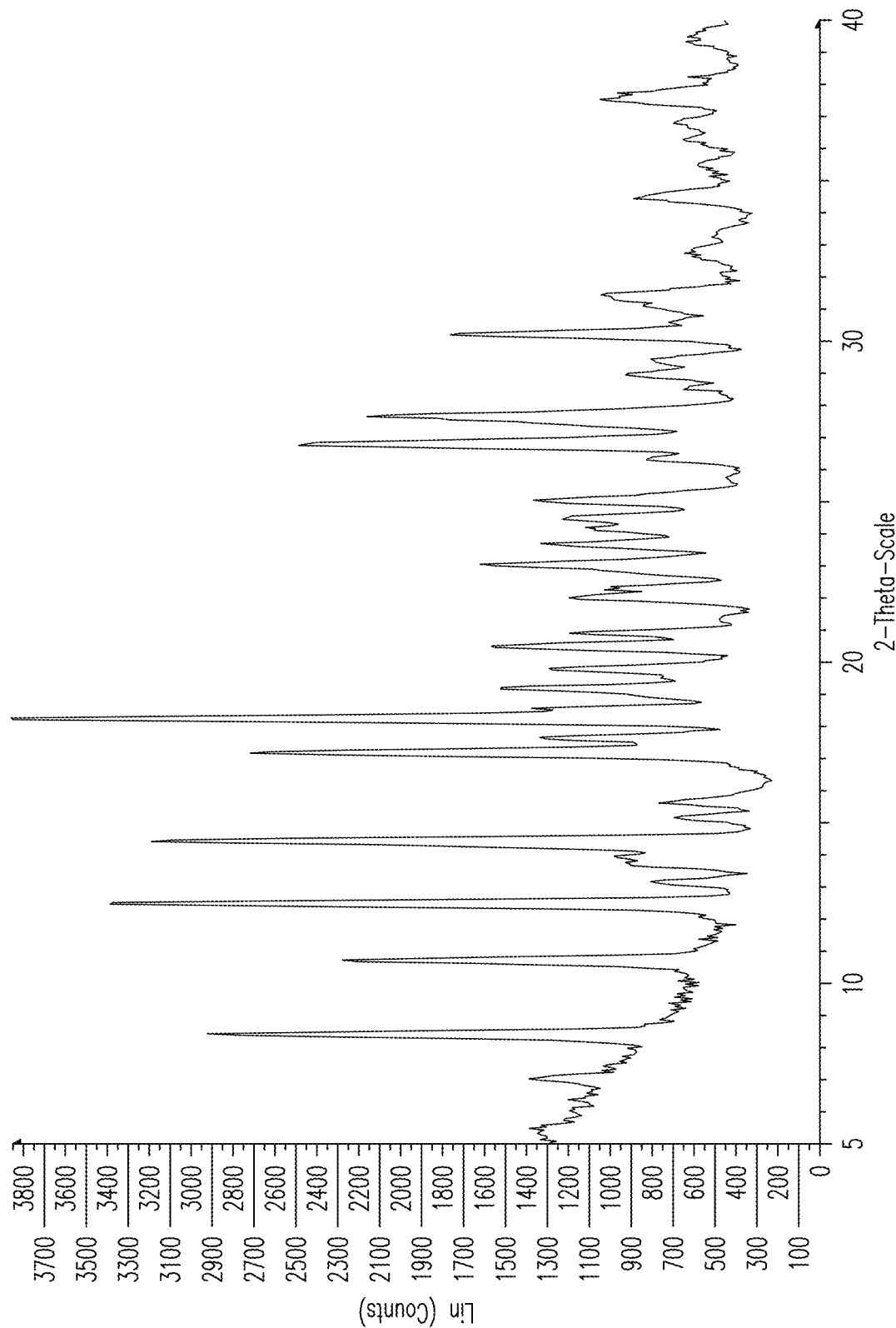
FIG. 1 illustrates the powder X-ray diffraction diagram of Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate.

In one embodiment, disclosed is 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Formula I)

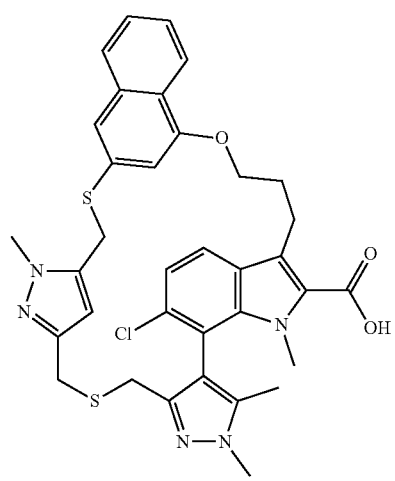

or a pharmaceutically acceptable salt thereof. In some aspects, disclosed is 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid. In some aspects, disclosed is a pharmaceutically acceptable salt of 17-chloro-5,13,14,22-tetramethyl-28-oxa-2,9-dithia-5,6,12,13,22-pentaazaheptacyclo[27.7.1.1$^{4,7}$.

$O^{11,15}.O^{16,21}.O^{20,24}.O^{30,35}$]octatriaconta-1(37),4(38),6,11,14,16,18,20,23,29,31,33,35-tridecaene-23-carboxylic acid.

In some embodiments, disclosed is $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Formula II)

(II)

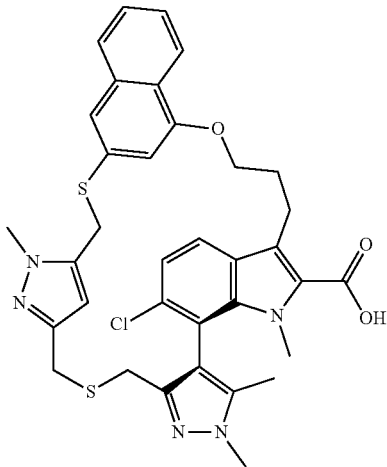

or a pharmaceutically acceptable salt thereof. In some aspects, disclosed is $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid. In some aspects, disclosed is a pharmaceutically acceptable salt of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid.

In some embodiments, disclosed is $(S_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Formula III)

(III)

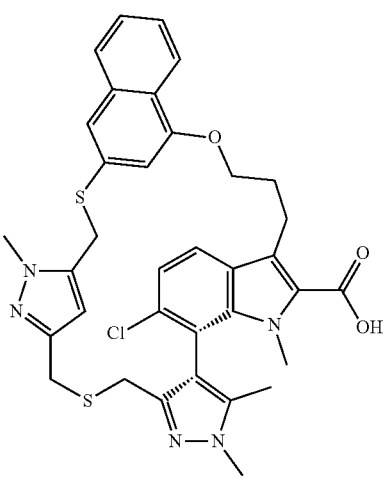

or a pharmaceutically acceptable salt thereof. In some aspects, disclosed is $(S_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid. In some aspects, disclosed is a pharmaceutically acceptable salt of $(S_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid.

The language "pharmaceutically acceptable salt" includes acid addition or base salts that retain the biological effectiveness and properties of the compounds of Formula (I), (II) and (III) and, which typically are not biologically or otherwise undesirable. In many cases, the compounds of Formula (I), (II) and (III) are capable of forming acid and/or base salts by virtue of the presence of basic and/or carboxyl groups or groups similar thereto. In one embodiment, the pharmaceutically acceptable salt includes quaternary ammonium salts.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulfate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, subsalicylate, sulfate/hydrogensulfate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic acid, sulfosalicylic acid, and the like.

Pharmaceutically acceptable base addition salts can be formed with inorganic and organic bases. Inorganic bases from which salts can be derived include, for example, ammonia and salts of ammonium and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine. In some aspects, the pharmaceutically acceptable salt of a compound of Formula (I), (II) or (III) is the sodium salt. In some aspects, the pharmaceutically acceptable salt of a compound of Formula (I), (II) or (III) is the meglumine salt.

The pharmaceutically acceptable salts of a compound of Formula (I), (II) or (III) can be synthesized from a basic or acidic moiety, by conventional chemical methods. Generally, such salts can be prepared by reacting free acid forms of these compounds with a stoichiometric amount of the appropriate base (such as Na$^+$, Ca$^{2+}$, Mg$^{2+}$, or K$^+$ hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., (1985); Berge et al., "*J. Pharm. Sci.,* 1977, 66, 1-19 and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms for a compound of Formula (I), (II) or (III). Isotopically labeled compounds have structures depicted by the formulas given herein except that one or more atoms are replaced by an atom of the same element but with differing mass number. Examples of isotopes that can be incorporated into the compounds of Formula (I), (II) and (III) and their salts include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{35}$S and $^{125}$I. The compounds of Formula (I), (II) and (III) may include various isotopically labeled compounds into which radioactive isotopes, such as, $^3$H, $^{11}$C, $^{14}$C, $^{35}$S and $^{36}$Cl are present. Isotopically labeled compounds of Formula (I), (II) and (III) can generally be prepared by conventional techniques known to those skilled in the art or by processes analogous to those described in the accompanying Examples using appropriate isotopically labeled reagents in place of the non-labeled reagents previously employed.

The compounds of Formula (I), (II) and (III) may have different isomeric forms. The language "optical isomer" or "stereoisomer" refers to any of the various stereoisomeric configurations which may exist for a given compound of Formula (I), (II) or (III). In particular, the compounds of Formula (I), (II) or (III) possess axial chirality, by virtue of restricted rotation around a biaryl bond and as such may exist as mixtures of enantiomers/atropisomers with enantiomeric excess between about 0% and >98% e.e. When a compound is a pure enantiomer, the stereochemistry at each chiral center may be specified by either $R_a$ or $S_a$. Such designations may also be used for mixtures that are enriched in one enantiomer. Further description of atropisomerism and axial chirality and rules for assignment of configuration can be found in Eliel, E. L. & Wilen, S. H. 'Stereochemistry of Organic Compounds' John Wiley and Sons, Inc. 1994. Resolved compounds whose absolute configuration is unknown can be designated (+) or (−) depending on the direction (dextro- or levorotatory) which they rotate plane polarized light at the wavelength of the sodium D line. The present disclosure is meant to include all such possible isomers, including racemic mixtures, optically pure forms and intermediate mixtures. Optically active ($R_a$)- and ($S_a$)- isomers may be prepared using chiral synthons, chiral reagents or chiral catalysts, or resolved using conventional techniques well known in the art, such as chiral HPLC.

Also disclosed herein the Intermediates 1-25 in the Examples, and salts thereof.

Solid Forms

In some embodiments, disclosed are solid forms of the compounds of Formula (I), (II) and (III), or a pharmaceutically acceptable salt thereof. The term "solid form" includes polymorphs, crystalline salts, solvates, hydrates and amorphous forms of the compounds of Formula (I), (II) or (III). The term "polymorph" includes crystalline materials that have the same chemical composition but different molecular packing. The language "crystalline salt" includes crystalline structures with the same chemical materials, but incorporating acid or base addition salts within the molecular packing of the crystalline structure. The term "solvate" includes crystalline structures of the same chemical material, but incorporating molecules of solvent within the molecular packing of the crystalline structure. The term "hydrates" includes crystalline structures of the same chemical material, but incorporating molecules of water within the molecular packing of the crystalline structure. The language "amorphous form" includes compounds of the same molecular material but without the molecular order of a crystalline structure (e.g., polymorph, crystalline salt, solvate or hydrate) of the same molecular material.

It is generally known that solid materials may be characterized using conventional techniques such as X-Ray Powder Diffraction (XRPD), Differential Scanning Calorimetry (DSC), Thermal Gravimetric Analysis (TGA), Diffuse Reflectance Infrared Fourier Transform (DRIFT) spectroscopy, Near Infrared (NIR) spectroscopy, solution and/or solid state nuclear magnetic resonance spectroscopy. The water content of such solid materials may be determined by Karl Fischer analysis.

The solid forms described herein provide XRPD patterns substantially the same as the XRPD patterns shown in the Figures, and have the various 2-theta (2θ) values as shown in the Tables included herein. One skilled in the art will understand that an XRPD pattern or diffractogram may be obtained which has one or more measurement errors depending on the recording conditions, such as the equipment or machine used. Similarly, it is generally known that intensities in an XRPD pattern may fluctuate depending on measurement conditions or sample preparation as a result of preferred orientation. Persons skilled in the art of XRPD will further realize that the relative intensity of peaks can also be affected by, for example, grains above 30 μm in size and non-unitary aspect ratios. The skilled person understands that the position of reflections can be affected by the precise height at which the sample sits in the diffractometer, and also the zero calibration of the diffractometer. The surface planarity of the sample may also have a small effect.

As a result of these considerations, the diffraction pattern data presented are not to be taken as absolute values (Jenkins, R & Snyder, R. L. 'Introduction to X-Ray Powder Diffractometry' John Wiley & Sons 1996; Bunn, C. W. (1948), 'Chemical Crystallography', Clarendon Press, London; Klug, H. P. & Alexander, L. E. (1974), 'X-Ray Diffraction Procedures'). It should also be understood that the solid forms embodied herein are not limited to those that provide XRPD patterns that are identical to the XRPD pattern shown in the Figures, and any solid forms providing XRPD patterns substantially the same as those shown in the Figures fall within the scope of the corresponding embodiment. A person skilled in the art of XRPD is able to judge the substantial identity of XRPD patterns. Generally, a measurement error of a diffraction angle in an XRPD is approximately 2θ (±0.2°), and such degree of a measurement error should be taken into account when considering the X-ray powder diffraction pattern in the Figures and when reading data contained in the Tables included herein.

A person skilled in the art also understands that the value or range of values observed in a particular compound's DSC thermogram will show variation between batches of different purities. Therefore, whilst for one compound the range may be small, for others the range may be quite large. Generally, a measurement error of a diffraction angle in DSC thermal events is approximately plus or minus 5° C., and such degree of a measurement error should be taken into account when considering the DSC data included herein. TGA thermograms show similar variations, such that a person skilled in the art recognizes that measurement errors should be taken into account when judging substantial identity of TGA thermograms.

In some embodiments, disclosed is a solid form of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, or a pharmaceutically acceptable salt thereof.

In some embodiments, disclosed is the amorphous form of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, or a pharmaceutically acceptable salt thereof.

Form A

In some embodiments, disclosed is Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has an XRPD pattern comprising at least one peak expressed as 2θ (±0.2°) at about 7.0°.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has an XRPD pattern comprising at least one peak expressed as 2θ (±0.2°) at about 8.4°.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has an XRPD pattern comprising at least one peak expressed as 2θ (±0.2°) at about 12.5°.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has an XRPD pattern comprising at least one peak expressed as 2θ (±0.2°) at about 7.0° and 8.4°.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has an XRPD pattern comprising at least one peak expressed as 2θ (±0.2°) at about 7.0° and 12.5°.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has an XRPD pattern comprising at least one peak expressed as 2θ (±0.2°) at about 8.4° and 12.5°.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has an XRPD pattern comprising at least one peak expressed as 2θ (±0.2°) at about 7.0°, 8.4° and 12.5°.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has an XRPD pattern comprising at least one peak expressed as 2θ (±0.2°) selected from about 5.4°, 7.0°, 8.4°, 10.7°, 12.5°, 13.1°, 14.4°, 15.1°, 15.6°, 17.1° and 18.2°.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has an XRPD pattern comprising at least one peak expressed as 2θ (±0.2°) selected from the peaks listed in Table 2.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has an XRPD pattern substantially similar to FIG. 1.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has a DSC thermogram comprising an endotherm with a desolvation onset at about 121° C. and a peak at about 152° C.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has a DSC thermogram comprising an endotherm with a melting/decomposition onset at about 181° C. and a peak at about 194° C.

Figure 2:
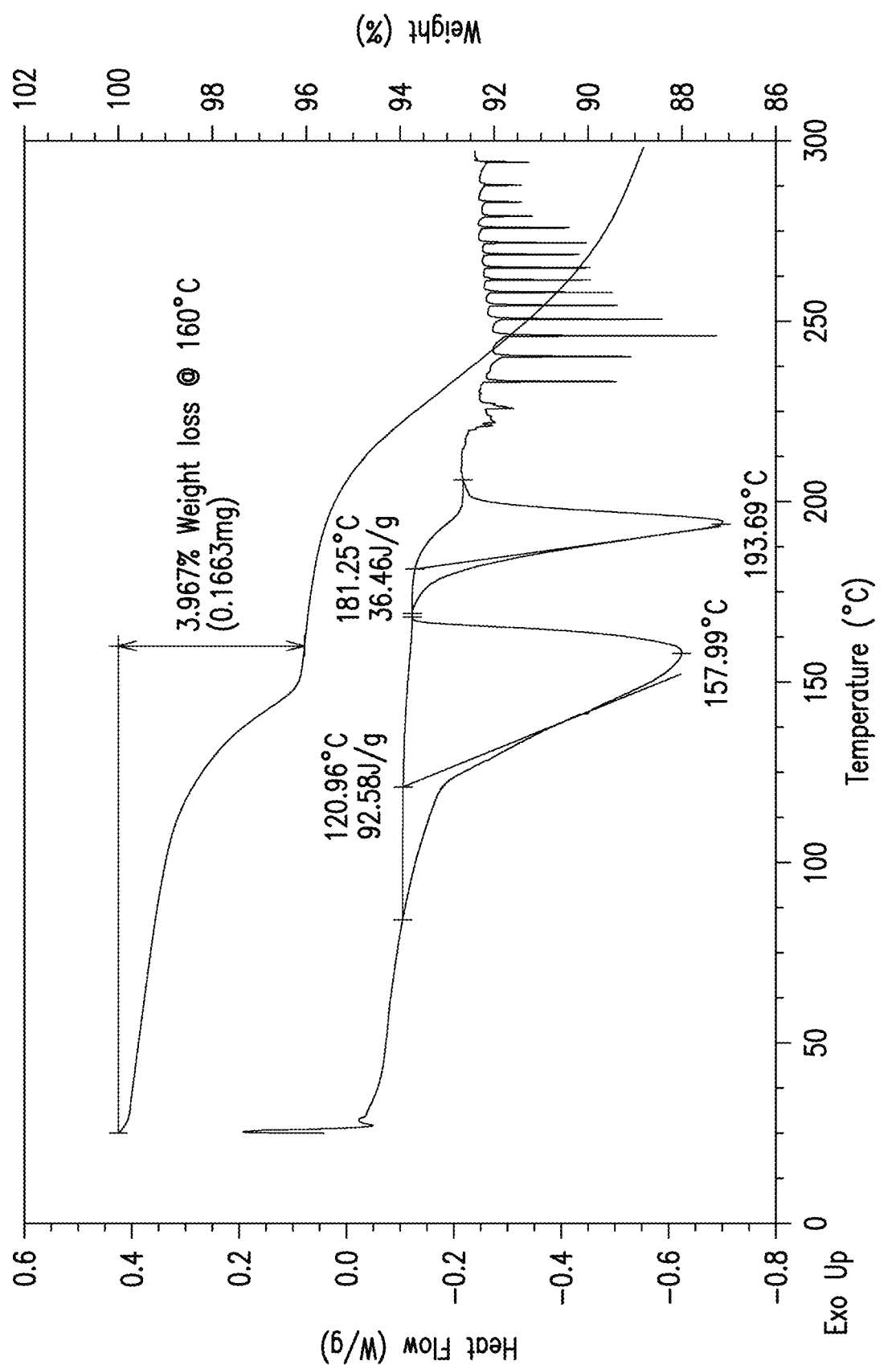
FIG. 2 illustrates the differential scanning calorimetry (DSC) and thermogravimetric analysis (TGA) traces of Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has a DSC pattern substantially similar to FIG. 2.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has a TGA thermogram exhibiting a mass loss of about 4.0% upon heating from about 25° C. to about 160° C.

In some embodiments, Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate has a TGA pattern substantially similar to FIG. 2.

Form B

In some embodiments, disclosed is Form B $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, methanol solvate Form C In some embodiments, disclosed is Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid.

In some embodiments, Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has an XRPD pattern comprising at least one peak expressed as 2θ (±0.2°) selected from about 5.1°, 6.8°, 8.1°, 10.1°, 12.0°, 14.1°, 14.8°, 15.3°, 16.5° and 17.2°.

In some embodiments, Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has an XRPD pattern comprising at least one peak expressed as 2θ (±0.2°) selected from the peaks listed in Table 3.

Figure 3:
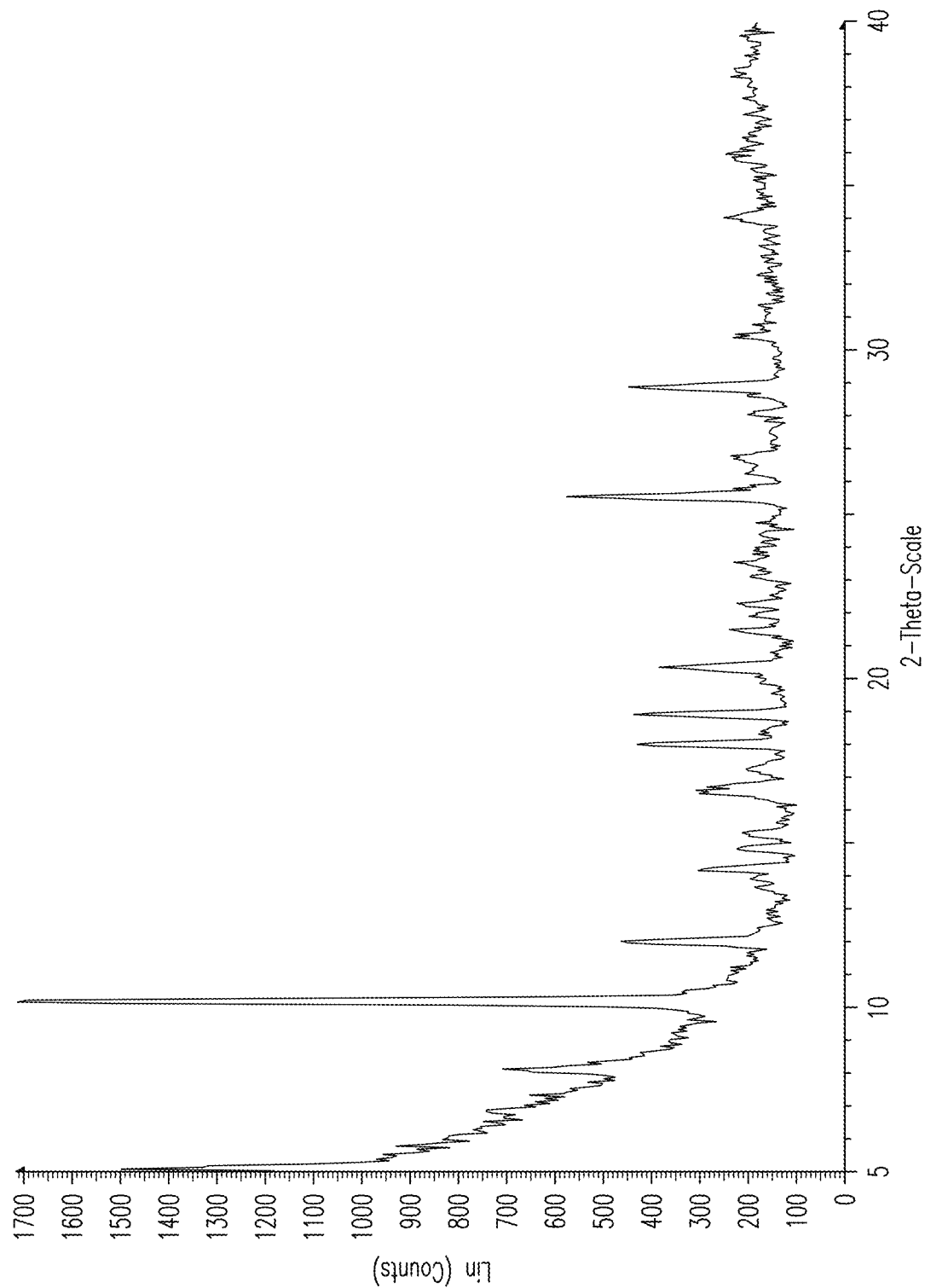
FIG. 3 illustrates the powder X-ray diffraction diagram of Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid.

In some embodiments, Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has an XRPD pattern substantially similar to FIG. 3.

In some embodiments, Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has a DSC thermogram comprising an endotherm with a desolvation onset at about 123° C. and a peak at about 140° C.

In some embodiments, Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has a DSC thermogram comprising an endotherm with a melting/decomposition onset at about 185° C. and a peak at about 196° C.

Figure 4:
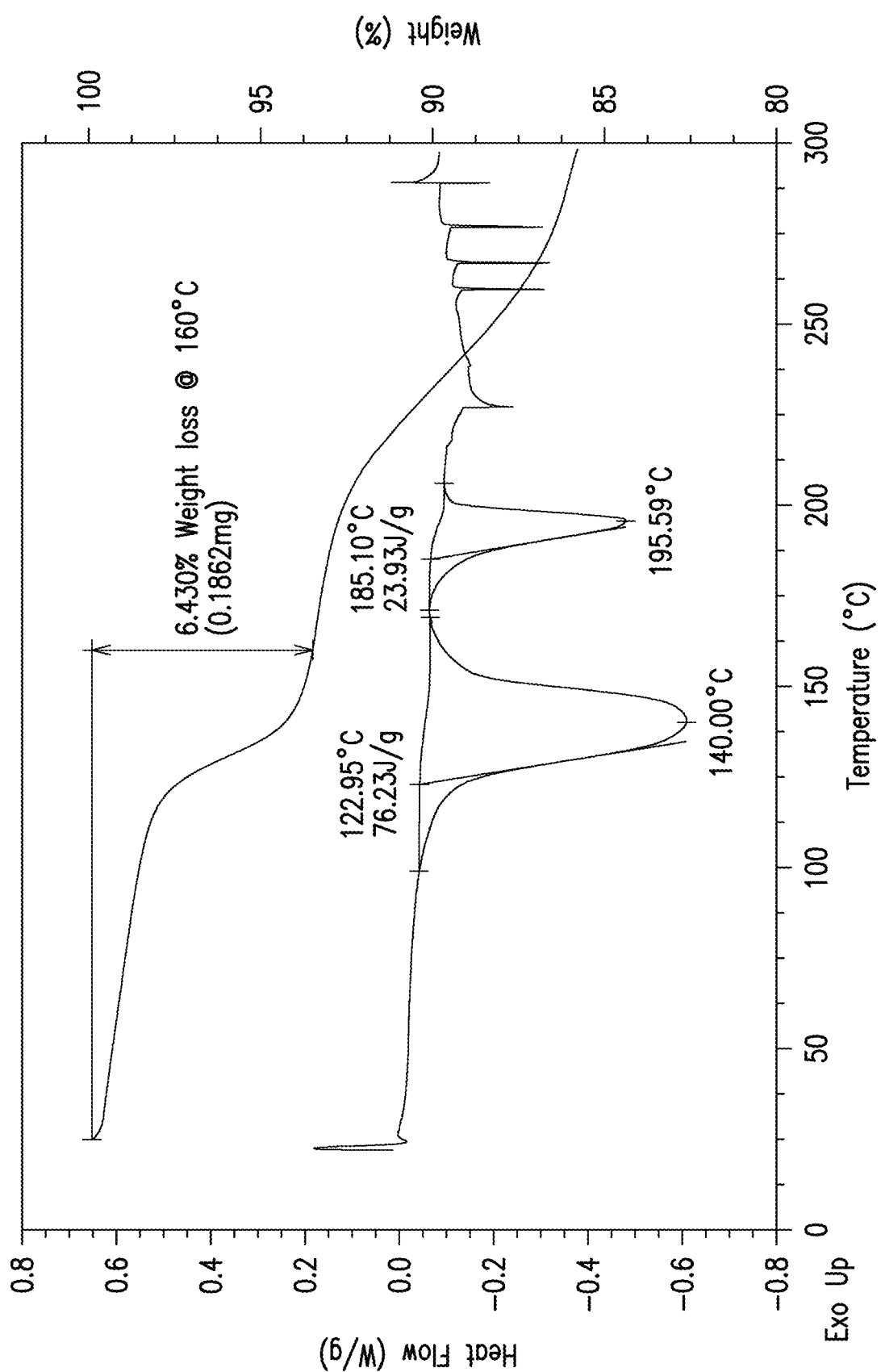
FIG. 4 illustrates the differential scanning calorimetry (DSC) and thermogravimetric analysis (TGA) traces of Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid.

In some embodiments, Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has a DSC pattern substantially similar to FIG. 4.

In some embodiments, Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has a TGA thermogram exhibiting a mass loss of about 6.4% upon heating from about 25° C. to about 160° C.

In some embodiments, Form C$(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has a TGA pattern substantially similar to FIG. 4.

Form D

In some embodiments, disclosed is Form D $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid.

In some embodiments, Form D $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has an XRPD pattern comprising at least one peak expressed as 2θ (±0.2°) selected from about 5.7°, 8.0°, 11.7°, 13.4°, 14.7°, 16.5°, 18.5°, 19.5° and 21.9°.

In some embodiments, Form D $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has an XRPD pattern comprising at least one peak expressed as 2θ (±0.2°) selected from the peaks listed in Table 4.

Figure 5:
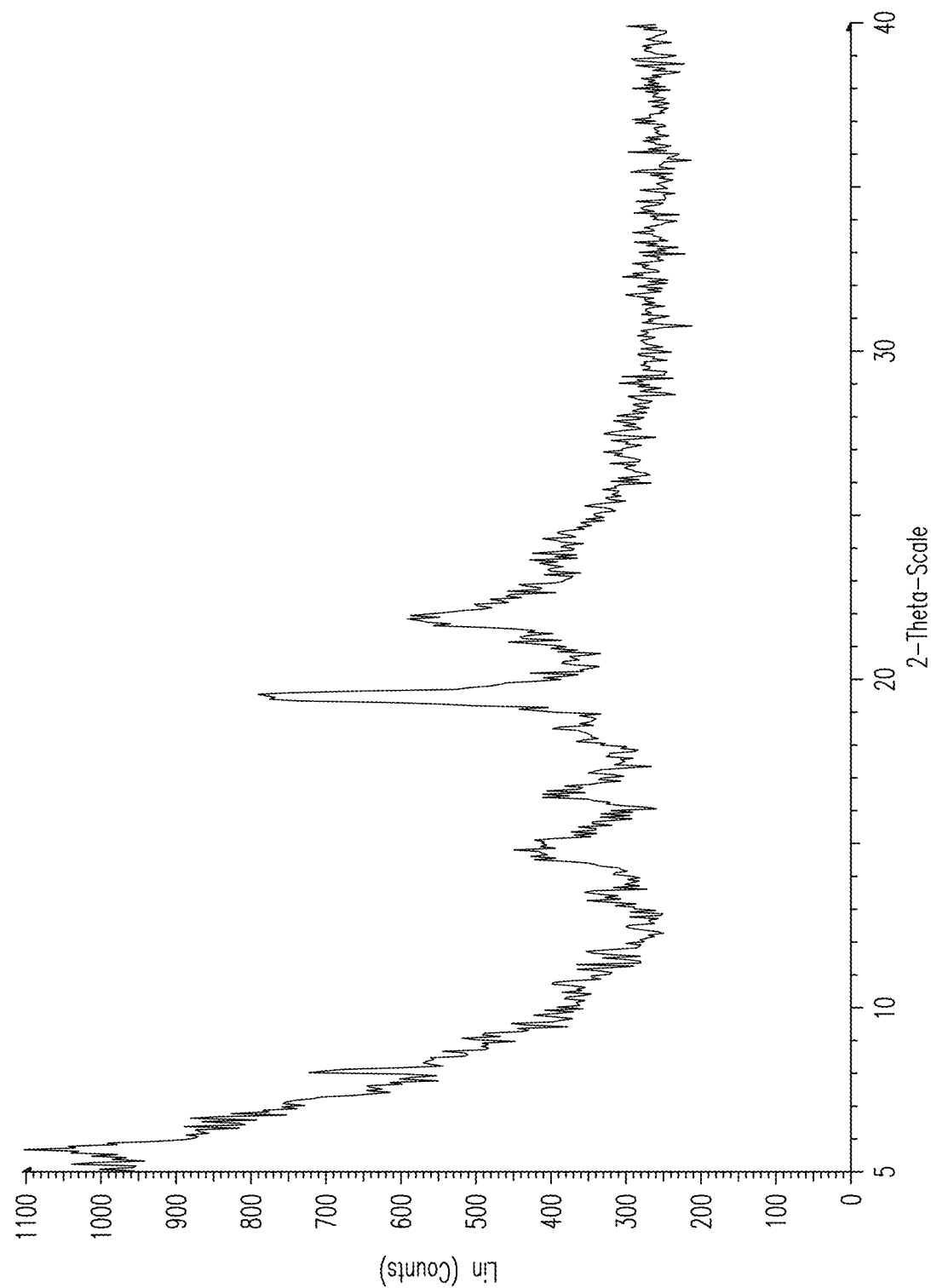
FIG. 5 illustrates the powder X-ray diffraction diagram of Form D $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid.

In some embodiments, Form D $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has an XRPD pattern substantially similar to FIG. 5.

In some embodiments, Form D $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has a DSC thermogram comprising an endotherm with a melting onset at about 156° C. and a peak at about 175° C.

Figure 6:
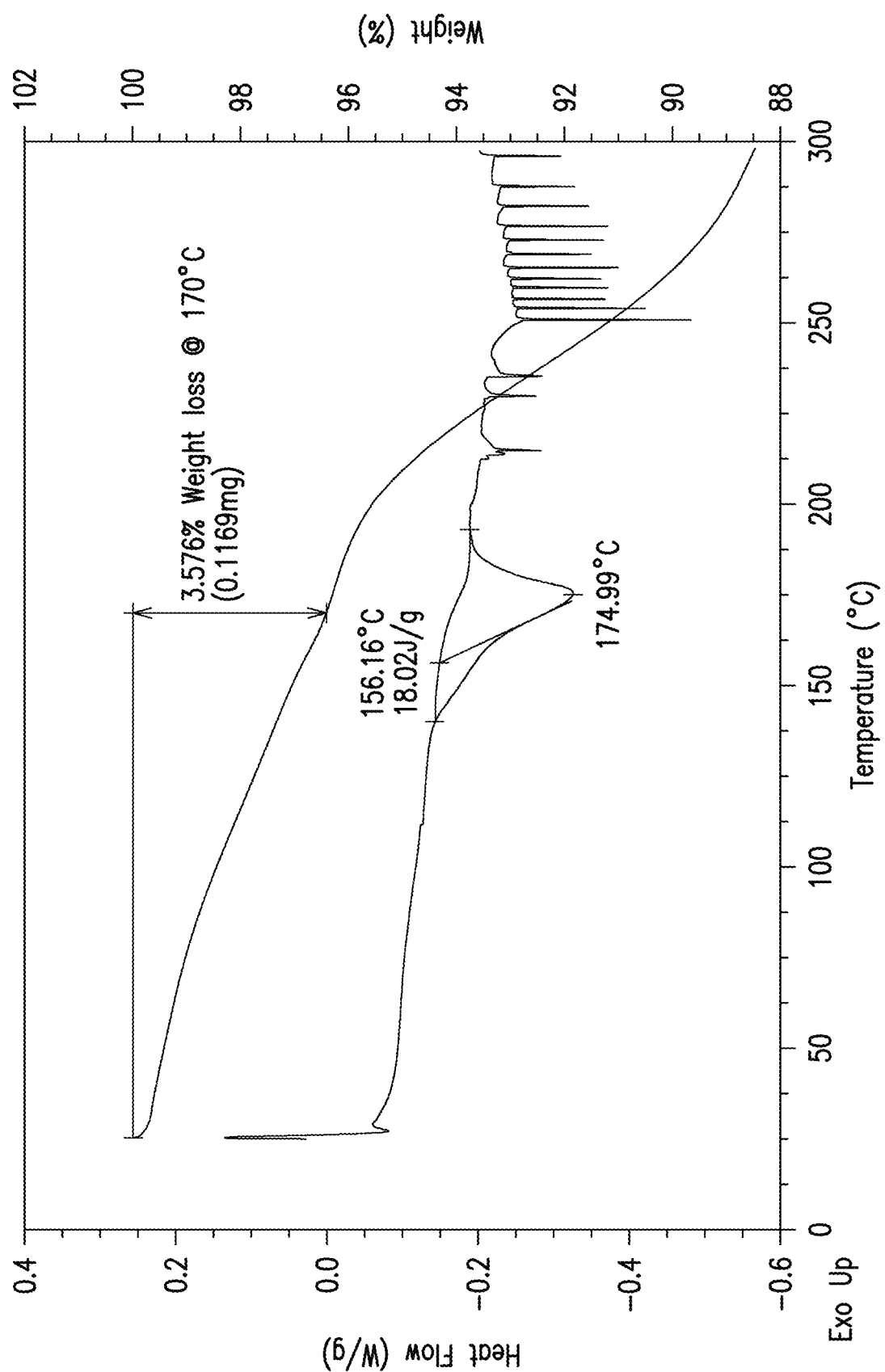
FIG. 6 illustrates the differential scanning calorimetry (DSC) and thermogravimetric analysis (TGA) traces of Form D $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid.

In some embodiments, Form D $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has a DSC pattern substantially similar to FIG. 6.

In some embodiments, Form D $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has a TGA thermogram exhibiting a mass loss of about 3.6% upon heating from about 25° C. to about 170° C.

In some embodiments, Form D $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has a TGA pattern substantially similar to FIG. 6.

Form E

In some embodiments, disclosed is Form E $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid.

In some embodiments, Form E $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has an XRPD pattern comprising at least one peak expressed as 2θ (±0.2°) selected from about 8.3°, 10.2°, 11.6°, 12.6°, 13.9°, 14.9°, 16.0°, 16.5°, 17.5° and 18.6°.

In some embodiments, Form E (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has an XRPD pattern comprising at least one peak expressed as 2θ (±0.2°) selected from the peaks listed in Table 5.

Figure 7:
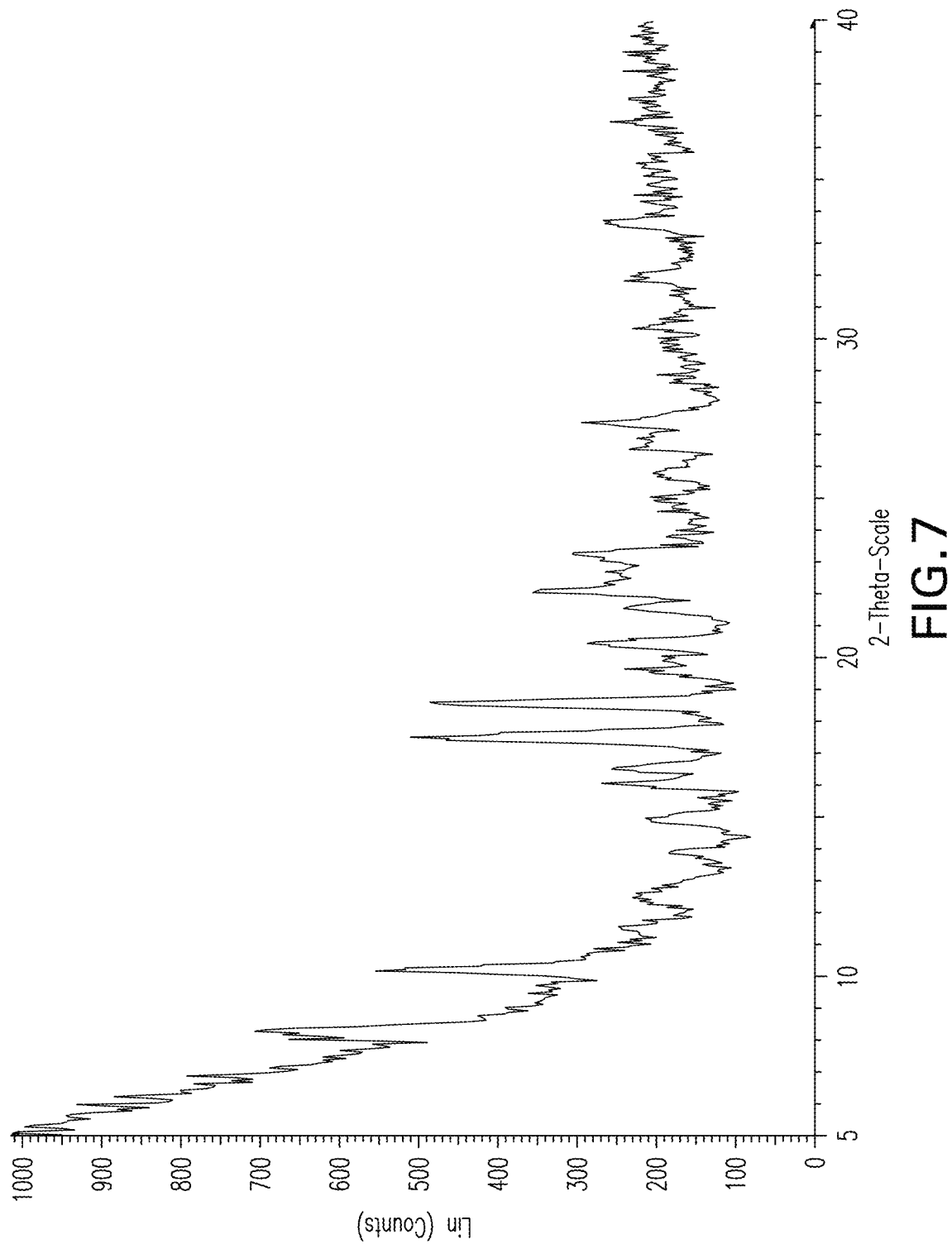
FIG. 7 illustrates the powder X-ray diffraction diagram of Form E $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$,0$^{16,21}$.0$^{20,24}$.0$^{30,35}$]octatriaconta-1(37),4(38),6,11,14,16,18,20,23,29,31,33,35-tridecaene-23-carboxylic acid.

In some embodiments, Form E (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid has an XRPD pattern substantially similar to FIG. 7.

Form F

In some embodiments, disclosed is Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has an XRPD pattern comprising at least one peak expressed as 2θ (±0.2°) at about 7.9°.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has an XRPD pattern comprising at least one peak expressed as 2θ (±0.2°) at about 11.9°.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has an XRPD pattern comprising at least one peak expressed as 2θ (±0.2°) at about 17.0°.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has an XRPD pattern comprising at least one peak expressed as 2θ (±0.2°) at about 7.9° and 11.9°.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has an XRPD pattern comprising at least one peak expressed as 2θ (±0.2°) at about 7.9° and 17.0°.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has an XRPD pattern comprising at least one peak expressed as 2θ (±0.2°) at about 11.9° and 17.0°.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has an XRPD pattern comprising at least one peak expressed as 2θ (±0.2°) at about 7.9°, 11.9° and 17.0°.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has an XRPD pattern comprising at least one peak expressed as 2θ (±0.2°) selected from about 5.4°, 7.9°, 10.6°, 11.9°, 12.9°, 14.3°, 14.9°, 15.7°, 17.0° and 18.9°.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has an XRPD pattern comprising at least one peak expressed as 2θ (±0.2°) selected from the peaks listed in Table 6.

Figure 8:
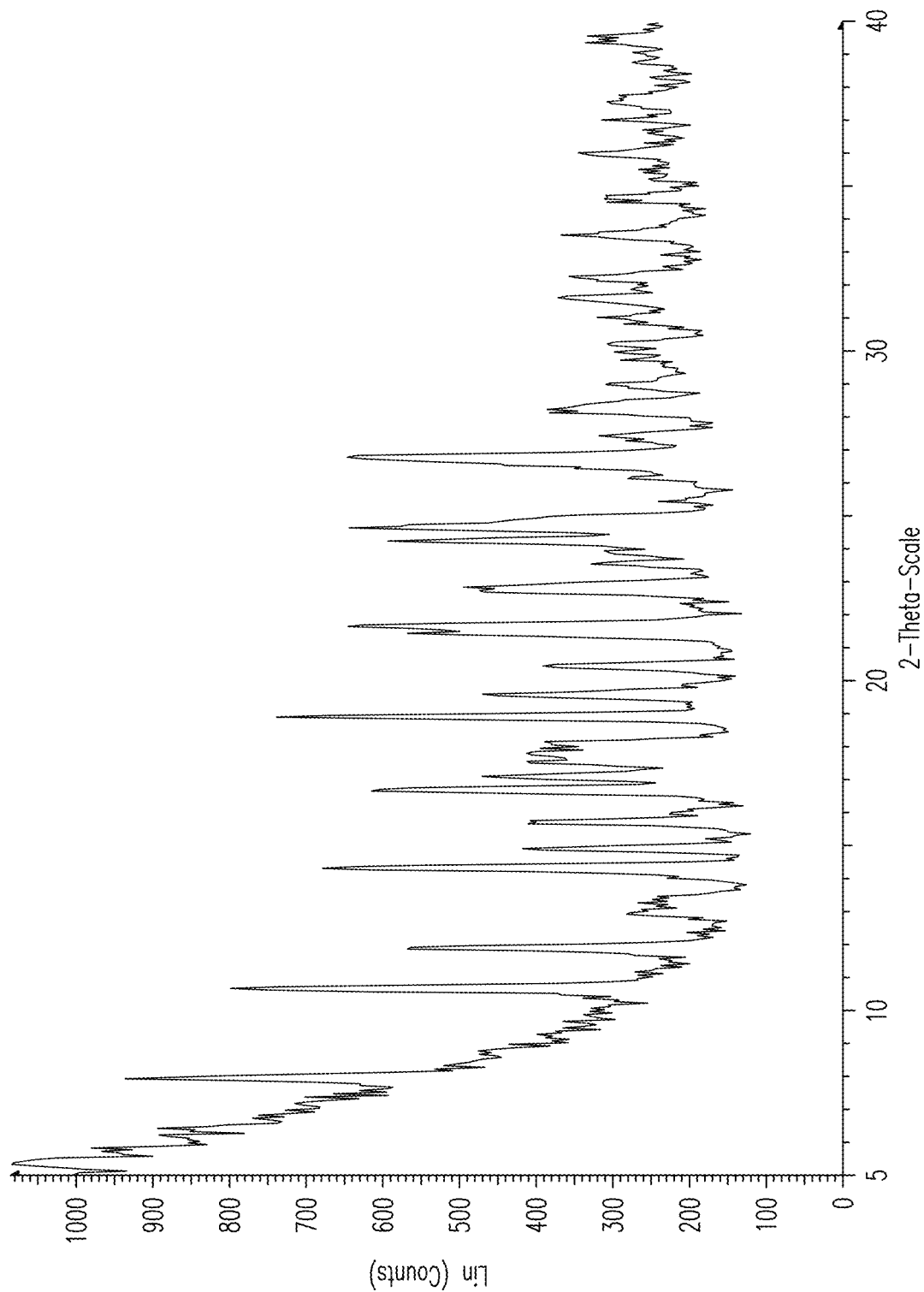
FIG. 8 illustrates the powder X-ray diffraction diagram of Form F $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has an XRPD pattern substantially similar to FIG. 8.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has a DSC thermogram comprising an endotherm with a desolvation onset at about 40° C. and a peak at about 67° C.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has a DSC thermogram comprising an endotherm with a melting/decomposition onset at about 185° C. and a peak at about 195° C.

Figure 9:
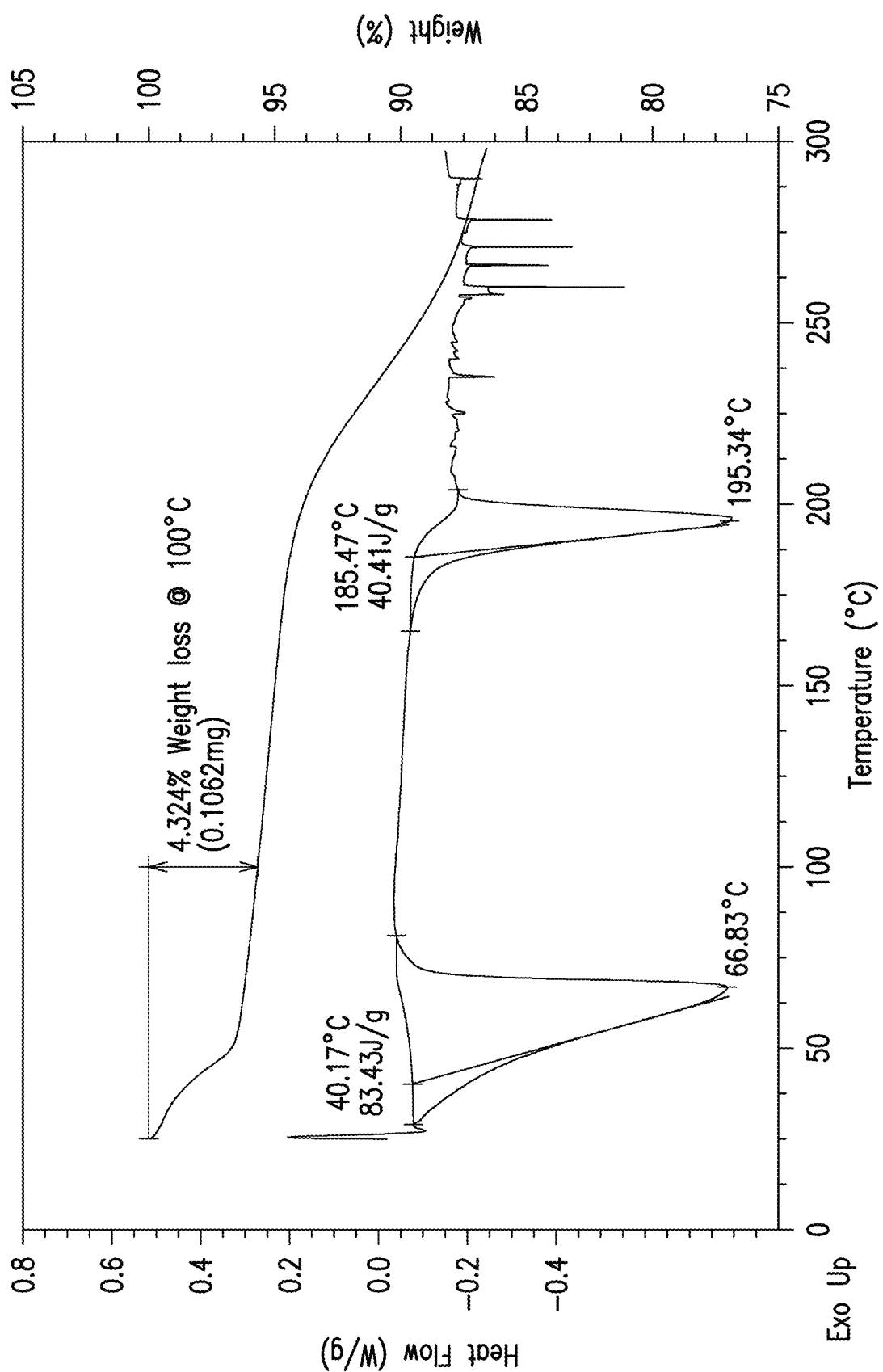
FIG. 9 illustrates the differential scanning calorimetry (DSC) and thermogravimetric analysis (TGA) traces of Form F $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has a DSC pattern substantially similar to FIG. 9.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has a TGA thermogram exhibiting a mass loss of about 4.3% upon heating from about 25° C. to about 100° C.

In some embodiments, Form F (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate has a TGA pattern substantially similar to FIG. 9.

Sodium Salt

In some embodiments, disclosed is (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, sodium salt.

In some embodiments, (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23- carboxylic acid, sodium salt has an XRPD pattern comprising at least one peak expressed as 2θ (±0.2°) selected from about 10.7°, 11.5°, 13.4°, 15.3°, 16.3°, 18.0°, 18.6°, 19.2°, 19.9° and 23.2°.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, sodium salt has an XRPD pattern comprising at least one peak expressed as 2θ (±0.2°) selected from the peaks listed in Table 7.

Figure 10:
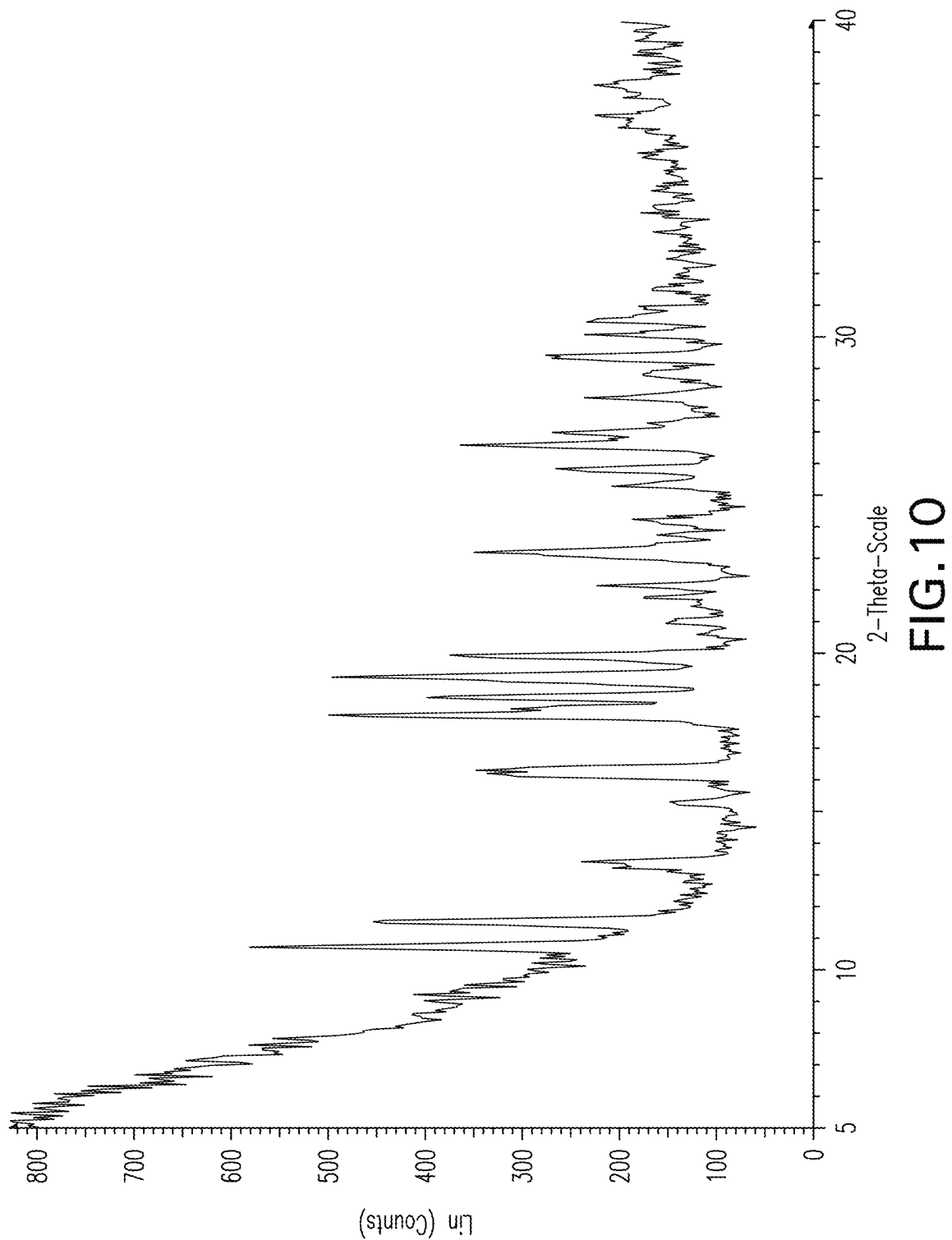
FIG. 10 illustrates the powder X-ray diffraction diagram of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid sodium salt.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, sodium salt has an XRPD pattern substantially similar to FIG. 10.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, sodium salt has a DSC thermogram comprising an endotherm with a broad desolvation onset at about 100° C. to about 200° C. In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, sodium salt has a DSC thermogram comprising an endotherm with a melting/decomposition onset at about 239° C. and a peak at about 246° C.

Figure 11:
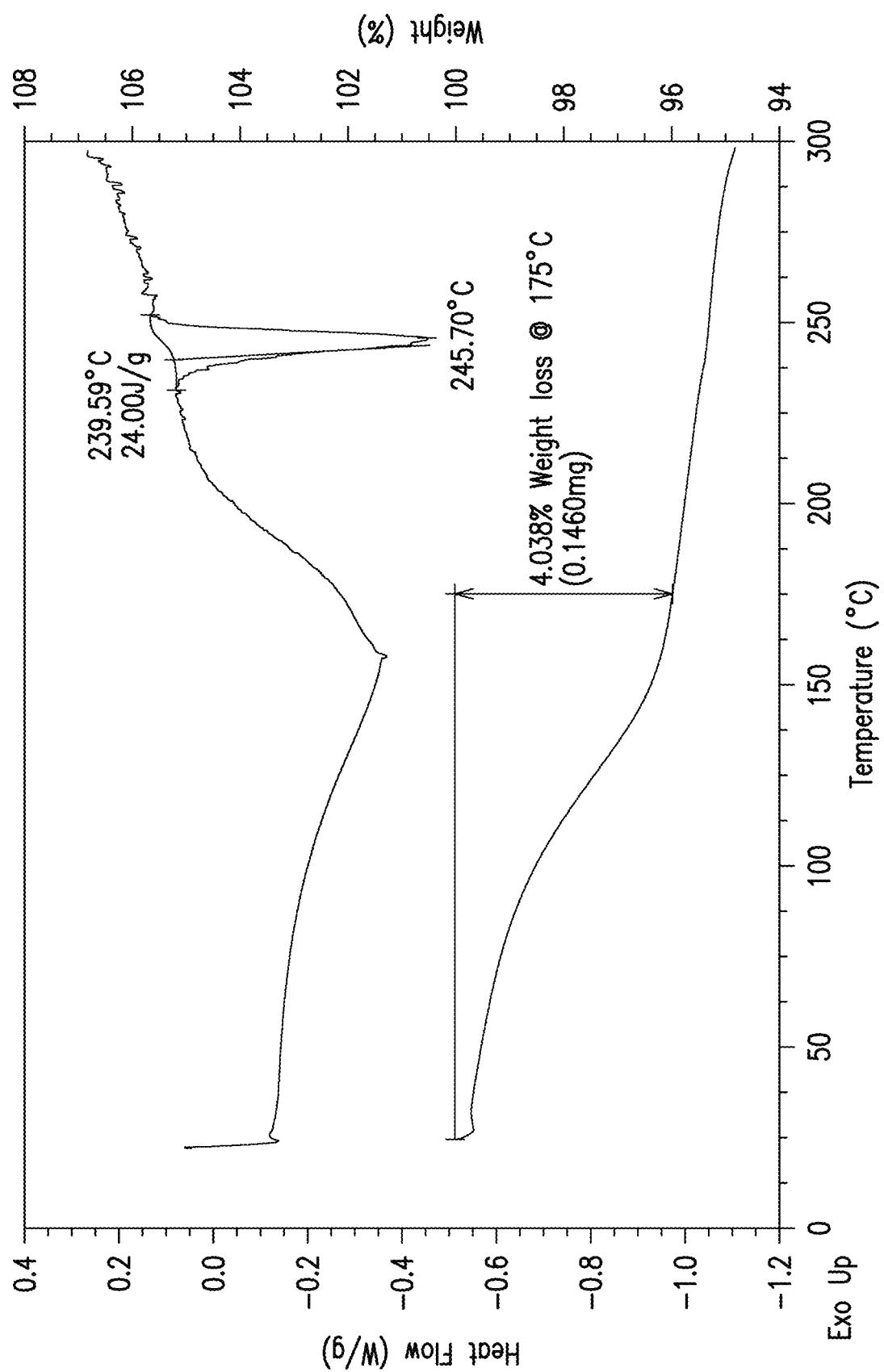
FIG. 11 illustrates the differential scanning calorimetry (DSC) and thermogravimetric analysis (TGA) traces of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid sodium salt.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, sodium salt has a DSC pattern substantially similar to FIG. 11.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, sodium salt has a TGA thermogram exhibiting a mass loss of about 4.0% upon heating from about 25° C. to about 175° C.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, sodium salt has a TGA pattern substantially similar to FIG. 11.

Meglumine Salt

In some embodiments, disclosed is $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, meglumine salt.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, meglumine salt has an XRPD pattern comprising at least one peak expressed as 2θ (±0.2°) selected from about 6.3°, 7.6°, 8.5°, 9.2°, 11.8°, 12.9°, 14.3°, 15.7° and 18.2°.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, meglumine salt has an XRPD pattern comprising at least one peak expressed as 2θ (±0.2°) selected from the peaks listed in Table 8.

Figure 12:
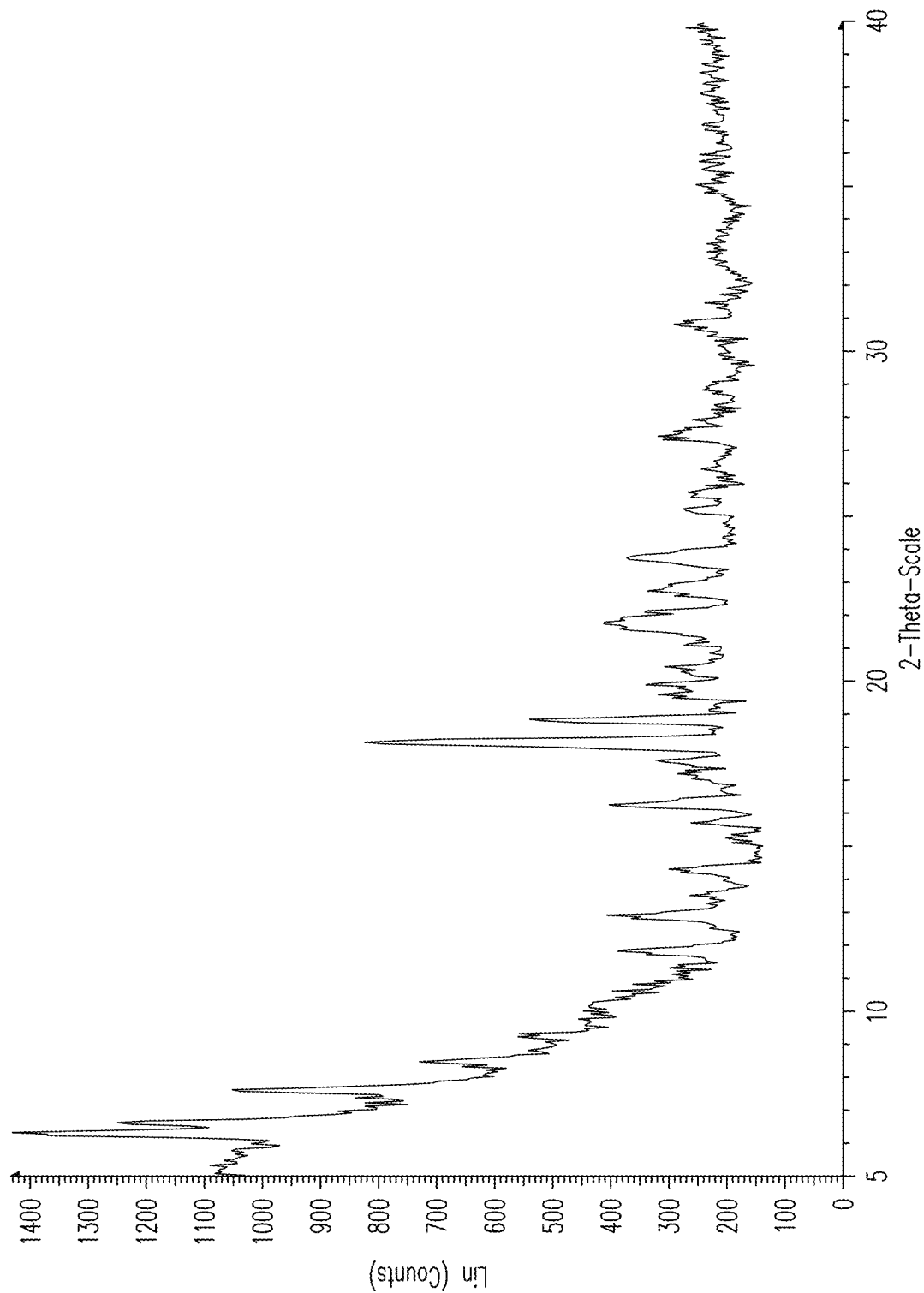
FIG. 12 illustrates the powder X-ray diffraction diagram of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid meglumine salt.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, meglumine salt has an XRPD pattern substantially similar to FIG. 12.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, meglumine salt has a DSC thermogram comprising an endotherm with a desolvation onset at about 69° C. and a peak at about 88° C. In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, meglumine salt has a DSC thermogram comprising an endotherm with a melting/decomposition onset at about 102° C. and a peak at about 104° C.

Figure 13:
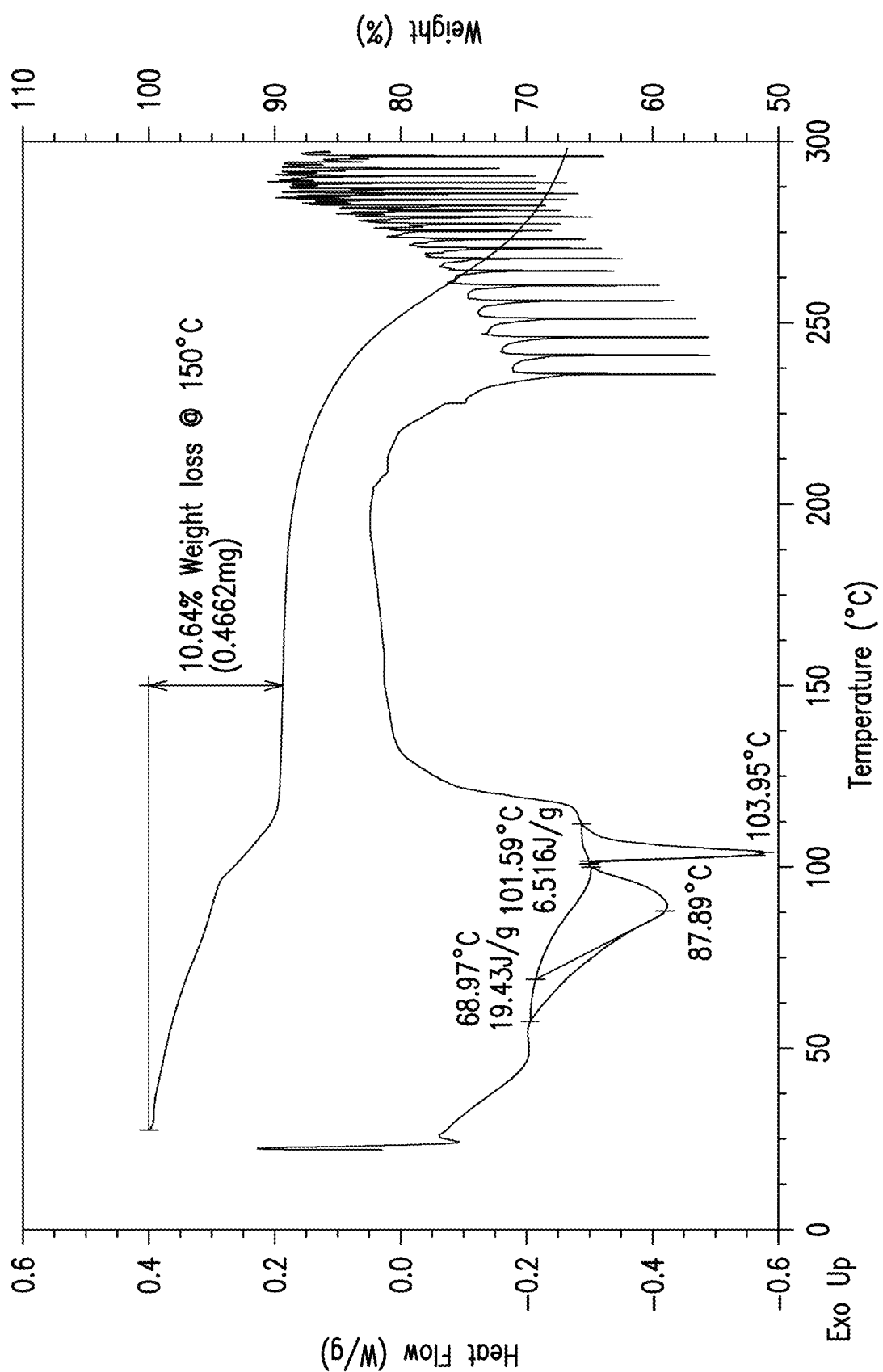
FIG. 13 illustrates the differential scanning calorimetry (DSC) and thermogravimetric analysis (TGA) traces of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid meglumine salt.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, meglumine salt has a DSC pattern substantially similar to FIG. 13.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, meglumine salt has a TGA thermogram exhibiting a mass loss of about 10.6% upon heating from about 25° C. to about 150° C.

In some embodiments, $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, meglumine salt has a TGA pattern substantially similar to FIG. 13.

Pharmaceutical Compositions

In some embodiments, disclosed are pharmaceutical compositions comprising a compound of Formula (I), (II) and (III), and a pharmaceutically acceptable excipient, carrier or diluent.

The language "pharmaceutically acceptable excipient, carrier or diluent" includes compounds, materials, compositions, and/or dosage forms which are, within the scope of sound medical judgment, suitable for use in contact with the tissues of human beings and animals without excessive toxicity, irritation, allergic response, or other problem or complication, as ascertained by one of skill in the art.

The disclosed compositions may be in a form suitable for oral use (for example, as tablets, lozenges, hard or soft capsules, aqueous or oily suspensions, emulsions, dispersible powders or granules, syrups or elixirs), for topical use (for example, as creams, ointments, gels, or aqueous or oily solutions or suspensions), for administration by inhalation (for example, as a finely divided powder or a liquid aerosol), for administration by insufflation (for example, as a finely divided powder) or for parenteral administration (for example, as a sterile aqueous or oily solution for intravenous, subcutaneous, intramuscular or intramuscular dosing or as a suppository for rectal dosing).

The disclosed compositions may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil, such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid; coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The compounds of Formula (I), (II) and (III) may be administered once, twice, three times a day or as many times in a 24 hour period as medically necessary. In some embodiments, the compounds of Formula (I), (II), and (III) may be administered daily, once a week, twice a week, 3 times a week, 4 times a week, 5 times a week or 6 times a week. One of skill in the art would readily be able to determine the amount of each individual dose based on the subject. In some embodiments, the compounds of Formula (I), (II) and (III) are administered in one dosage form. In some embodiments, the compounds of Formula (I), (II) and (III) are administered in multiple dosage forms.

Method of Use

In one aspect, disclosed are methods for treating cancer in a subject in need thereof, comprising administering to the subject an effective amount of a compound of Formula (I), (II) or (III), or a pharmaceutically acceptable salt thereof.

In one aspect, disclosed is a compound of Formula (I), (II) or (III), or a pharmaceutically acceptable salt thereof, for use in treating cancer.

In one aspect, disclosed is the use of a compound of Formula (I), (II) or (III), or a pharmaceutically acceptable salt thereof, in the manufacture of a medicament for treating a cancer.

In one aspect, disclosed are pharmaceutical compositions comprising a compound of Formula (I), (II) or (III), or a pharmaceutically acceptable salt thereof, for use in treating cancer.

The term "cancer" includes, but is not limited to, hematological malignancies such as acute myeloid leukemia, multiple myeloma, mantle cell lymphoma, chronic lymphocytic leukemia, diffuse large B cell lymphoma, Burkitt's lymphoma, follicular lymphoma and solid tumors, for example, non-small cell lung cancer (NSCLC), small cell lung cancer (SCLC), breast cancer, neuroblastoma, prostate cancer, melanoma, pancreatic cancer, uterine, endometrial and colon cancer.

In one aspect, disclosed are methods for treating multiple myeloma in a subject in need thereof, comprising administering to the subject an effective amount of a compound of Formula (I), (II) or (III), or a pharmaceutically acceptable salt thereof.

In one aspect, disclosed is a compound of Formula (I), (II) or (III), or a pharmaceutically acceptable salt thereof, for use in treating multiple myeloma.

In one aspect, disclosed is the use of a compound of Formula (I), (II) or (III), or a pharmaceutically acceptable salt thereof, in the manufacture of a medicament for treating a multiple myeloma.

In one aspect, disclosed are pharmaceutical compositions comprising a compound of Formula (I), (II) or (III), or a pharmaceutically acceptable salt thereof, for use in treating multiple myeloma.

In one aspect, disclosed are methods for treating acute myeloid leukemia in a subject in need thereof, comprising administering to the subject an effective amount of a compound of Formula (I), (II) or (III), or a pharmaceutically acceptable salt thereof.

In one aspect, disclosed is a compound of Formula (I), (II) or (III), or a pharmaceutically acceptable salt thereof, for use in treating acute myeloid leukemia.

In one aspect, disclosed is the use of a compound of Formula (I), (II) or (III), or a pharmaceutically acceptable salt thereof, in the manufacture of a medicament for treating a acute myeloid leukemia.

In one aspect, disclosed are pharmaceutical compositions comprising a compound of Formula (I), (II) or (III), or a pharmaceutically acceptable salt thereof, for use in treating acute myeloid leukemia.

In one aspect, disclosed are methods for treating cancer in a subject in need thereof comprising administering to the subject an effective amount of a compound of Formula (I), (II) or (III), or a pharmaceutically acceptable salt thereof in combination with an anti-cancer agent, or a pharmaceutically acceptable salt thereof.

In one aspect, disclosed is a compound of Formula (I), (II) or (III), or a pharmaceutically acceptable salt thereof in combination with anti-cancer agent, or a pharmaceutically acceptable salt thereof, for use in treating a cancer.

In one aspect, disclosed is the use of a compound of Formula (I), (II) or (III), or a pharmaceutically acceptable salt thereof, in combination with an anti-cancer agent, or a pharmaceutically acceptable salt thereof, in the manufacture of a medicament for treating cancer.

In one aspect, disclosed are pharmaceutical compositions comprising a compound of Formula (I), (II) or (III), or a pharmaceutically acceptable salt thereof, in combination with an anti-cancer agent, or a pharmaceutically acceptable salt thereof, for use in treating cancer.

The language "in combination with" includes administering the compound of Formula (I), (II) or (III), or a pharmaceutically acceptable salt thereof, and the anti-cancer agent, or pharmaceutically acceptable salt thereof, sequentially, separately or simultaneously. In some aspects, the compound of Formula (I), (II) or (III), or a pharmaceutically acceptable salt thereof, and the anti-cancer agent, or pharmaceutically acceptable salt thereof, are administered in the same formulation, for example, in a fixed dose formulation. In some embodiments, the compound of Formula (I), (II) or (III), or a pharmaceutically acceptable salt thereof, and the anti-cancer agent, or pharmaceutically acceptable salt thereof, are administered in separate formulations, and are administered at substantially the same time, sequentially or separately.

The language "anti-cancer agent" includes, but is not limited to, radiation, alkylating agents, angiogenesis inhibitors, antibodies, antibody-drug conjugates, antimetabolites, antimitotics, antiproliferatives, antivirals, aurora kinase inhibitors, other cell death activators (for example, inhibitors of Bcl-2, Bcl-xL, Bcl-w, Bfl-1), activators of death receptor pathways (for example, FAS or TRAIL agonists), Bcr-Abl kinase inhibitors, BET (bromodomain) inhibitors, BiTE (Bi-Specific T cell Engager) antibodies, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, EGFR inhibitors, heat shock protein (HSP) inhibitors, histone deacetylase (HDAC) inhibitors, hormonal therapies, immunologicals, inhibitors of the inhibitors of apoptosis proteins (IAPs), intercalating antibiotics, kinase inhibitors, kinesin inhibitors, Jak2 inhibitors, mammalian target of rapamycin (mTOR) inhibitors, microRNA's, mitogen-activated extracellular signal-regulated kinase (MEK) inhibitors, BRAF inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, and ubiquitin ligase inhibitors. Disclosed herein are combinations of any of the compounds of Formula (I), (II) or (III) and an anti-cancer agent.

Alkylating agents include altretamine, AMD-473, AP-5280, apaziquone, bendamustine, brostallicin, busulfan, cisplatin, carboplatin, carboquone, carmustine (BCNU), chlorambucil, CLORETAZINE® (laromustine, VNP 40101 M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, nitrosoureas, oxaliplatin, ranimustine, temozolomide, thiotepa, TREANDA® (bendamustine), treosulfan, rofosfamide and the like.

Angiogenesis inhibitors include endothelial-specific receptor, (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors, ALK inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, pemextred, raltitrexed, Ribavirin, triapine, trimetrexate, S-1, tiazofurin, tegafur, TS-1, vidarabine, UFT and the like.

Bcl-2 protein inhibitors include ABT-199, AT-101 ((−) gossypol), GENASENSE® (G3139 or oblimersen (Bcl-2-targeting antisense oligonucleotide)), IPI-194, IPI-565, ABT-737, ABT-263, GX-070 (obatoclax) and the like.

Btk inhibitors include ibrutinib and acalabrutinib and the like.

Bromodomain inhibitors include I-BET 762, OTX-015, CPI-203, LY294002 and the like. CDK inhibitors include BMI-1040, BMS-032, BMS-387, CVT-2584, flavopiridol, GPC-286199, MCS-5A, PD0332991, PHA-690509, seliciclib (CYC-202, R-roscovitine), ZK-304709 and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib), TAGRISSO (AZD9291), and the like.

ALK inhibitors include crizotinib, ceritinib, and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 bifunctional bispecific antibodies, mAB AR-209, mAB 2B-1 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like.

Kinesin inhibitors include Eg5 inhibitors such as AZD4877, ARRY-520; CENPE inhibitors such as GSK923295A and the like.

MEK inhibitors include trametinib (GSK1120212), binimetinib (MEK162), selumetinib (AZD6244), cobimetinib (XL518), ARRY-142886, ARRY-438162, PD-325901, PD-98059, and the like.

BRAF inhibitors include sorafenib, vemurafenib, dabrafenib, GDC-0879, LGX818 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

VEGFR inhibitors include AVASTIN (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptanib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antitumor antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Inhibitors of DNA repair mechanisms such as CHK kinase; DNA-dependent protein kinase inhibitors; inhibitors of poly (ADP-ribose) polymerase (PARP inhibitors) including ABT-888 (veliparib), olaparib, KU-59436, AZD-2281, AG-014699, BSI-201, BGP-15, INO-1001, ONO-2231 and the like; and Hsp90 inhibitors such as tanespimycin and retaspimycin.

Proteasome inhibitors include VELCADE® (bortezomib), KYPROLIS (carfilzomib), NINLARO (ixazomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-lbritumomab tiuxetan) and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Additionally, compounds of Formula (I), (II) and (III) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestain A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-*pseudomonas* exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

In one aspect, disclosed are methods for treating cancer in a subject in need thereof comprising administering to the subject an effective amount of a compound of Formula (I), (II) or (III), or a pharmaceutically acceptable salt thereof in combination with bortezomib, or a pharmaceutically acceptable salt thereof.

In one aspect, disclosed is a compound of Formula (I), (II) or (III), or a pharmaceutically acceptable salt thereof in combination with bortezomib, or a pharmaceutically acceptable salt thereof, for use in treating a cancer.

In one aspect, disclosed is the use of a compound of Formula (I), (II) or (III), or a pharmaceutically acceptable salt thereof, in combination with bortezomib, or a pharmaceutically acceptable salt thereof, in the manufacture of a medicament for treating cancer.

In one aspect, disclosed are pharmaceutical compositions comprising a compound of Formula (I), (II) or (III), or a pharmaceutically acceptable salt thereof, in combination with bortezomib, or a pharmaceutically acceptable salt thereof, for use in treating cancer.

In one aspect, disclosed are methods for treating multiple myeloma in a subject in need thereof comprising administering to the subject an effective amount of a compound of Formula (I), (II) or (III), or a pharmaceutically acceptable salt thereof in combination with bortezomib, or a pharmaceutically acceptable salt thereof.

In one aspect, disclosed is a compound of Formula (I), (II) or (III), or a pharmaceutically acceptable salt thereof in combination with bortezomib, or a pharmaceutically acceptable salt thereof, for use in treating multiple myeloma.

In one aspect, disclosed is the use of a compound of Formula (I), (II) or (III), or a pharmaceutically acceptable salt thereof, in combination with bortezomib, or a pharmaceutically acceptable salt thereof, in the manufacture of a medicament for treating multiple myeloma.

In one aspect, disclosed are pharmaceutical compositions comprising a compound of Formula (I), (II) or (III), or a pharmaceutically acceptable salt thereof, in combination with bortezomib, or a pharmaceutically acceptable salt thereof, for use in treating multiple myeloma.

In one aspect, disclosed are methods for inhibiting Mcl-1 in a subject in need thereof, comprising administering to the subject an effective amount of a compound of Formula (I), (II) or (III), or a pharmaceutically acceptable salt thereof.

In one aspect, disclosed is a compound of Formula (I), (II) or (III), or a pharmaceutically acceptable salt thereof, for use in inhibiting Mcl-1

In one aspect, disclosed is the use of a compound of Formula (I), (II) or (III), or a pharmaceutically acceptable salt thereof, in the manufacture of a medicament for inhibiting Mcl-1.

In one aspect, disclosed are pharmaceutical compositions comprising a compound of Formula (I), (II) or (III), or a pharmaceutically acceptable salt thereof, for use in inhibiting Mcl-1.

The term "Mcl-1" refers to Myeloid Cell Leukemia 1, an anti-apoptotic member of the BCL-2 family of proteins.

The language "effective amount" includes an amount of a compound of Formula (I), (II) or (III) that will elicit a biological or medical response in a subject, for example, the reduction or inhibition of enzyme or protein activity related to Mcl-1 or cancer; amelioration of symptoms of cancer; or the slowing or delaying of progression of cancer. In some embodiments, the language "effective amount" includes the amount of a compound of Formula (I), (II) or (III), that when administered to a subject, is effective to at least partially alleviate, inhibit, and/or ameliorate cancer or inhibit Mcl-1, and/or reduce or inhibit the growth of a tumor or proliferation of cancerous cells in a subject.

The term "subject" includes warm-blooded mammals, for example, primates, dogs, cats, rabbits, rats, and mice. In some embodiments, the subject is a primate, for example, a human. In some embodiments, the subject is suffering from cancer. In some embodiments, the subject is in need of treatment (e.g., the subject would benefit biologically or medically from treatment).

The language "inhibit," "inhibition" or "inhibiting" includes a decrease in the baseline activity of a biological activity or process. In some embodiments, the compounds of Formula (I), (II) or (III) inhibit Mcl-1.

The language "treat," "treating" and "treatment" includes the reduction or inhibition of enzyme or protein activity related to Mcl-1 or cancer in a subject, amelioration of one or more symptoms of cancer in a subject, or the slowing or delaying of progression of cancer in a subject. The language "treat," "treating" and "treatment" also includes the reduction or inhibition of the growth of a tumor or proliferation of cancerous cells in a subject.

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless Stated Otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation or utilizing Genevac equipment or Biotage v10 evaporator under reduced pressure;

(iii) silica gel chromatography purifications were performed on an automated Teledyne Isco CombiFlash® Rf or Teledyne Isco CombiFlash® Companion® using prepacked RediSep Rf Gold™ Silica Columns (20-40 μm, spherical particles), GraceResolv™ Cartridges (Davisil® silica) or Silicycle cartridges (40-63 μm).

(iv) chiral preparative chromatography was performed on a Waters Prep 100 SFC-MS instrument with MS- and UV-triggered collection or a Thar MultiGram III SFC instrument with UV collection.

(v) chiral analytical chromatography was performed on either a Waters X5 SFC-MS with UV detection or a Waters UPC2 SFC-MS with UV and ELSD detection.

(vi) yields, where present, are not necessarily the maximum attainable;

(vii) in general, the structures of end-products of the Formula I were confirmed by NMR spectroscopy; NMR chemical shift values were measured on the delta scale, using the solvent residual peak as the internal standard [proton magnetic resonance spectra were determined using a Bruker Avance 500 (500 MHz), Bruker Avance 400 (400 MHz), Bruker Avance 300 (300 MHz) or Bruker DRX (300 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal; ABq, AB quartet.

(viii) in general, end-products of the Formula I were also characterized by mass spectroscopy following liquid chromatography (UPLC); using a Waters UPLC fitted with a Waters SQ mass spectrometer (Column temp 40° C., UV=220-300 nm or 190-400 nm, Mass Spec=ESI with positive/negative switching) at a flow rate of 1 mL/min using a solvent system of 97% A+3% B to 3% A+97% B over 1.50 min (total run time with equilibration back to starting conditions, etc., 1.70 min), where A=0.1% formic acid or 0.05% trifluoroacetic acid in water (for acidic work) or 0.1% ammonium hydroxide in water (for basic work) and B=acetonitrile. For acidic analysis the column used was a Waters Acquity HSS T3 (1.8 μm, 2.1×50 mm), for basic analysis the column used was a Waters Acquity BEH C18 (1.7 μm, 2.1×50 mm). Alternatively, UPLC was carried out using a Waters UPLC fitted with a Waters SQ mass spectrometer (Column temp 30° C., UV=210-400 nm, Mass Spec=ESI with positive/negative switching) at a flow rate of 1 mL/min using a solvent gradient of 2 to 98% B over 1.5 min (total run time with equilibration back to starting conditions 2 min), where A=0.1% formic acid in water and B=0.1% formic acid in acetonitrile (for acidic work) or A=0.1% ammonium hydroxide in water and B=acetonitrile (for basic work). For acidic analysis the column used was a Waters Acquity HSS T3 (1.8 μm, 2.1×30 mm), for basic analysis the column used was a Waters Acquity BEH C18 (1.7 μm, 2.1×30 mm); The reported molecular ion corresponds to the [M+H]+ unless otherwise specified; for molecules with multiple isotopic patterns (Br, Cl, etc.) the reported value is the one obtained with highest intensity unless otherwise specified.

(x) intermediate purity was assessed by thin layer chromatographic, mass spectroscopy, LCMS, UPLC/MS, HPLC and/or NMR analysis;

(xi) the following abbreviations have been used:

ACN acetonitrile aq. aqueous conc. concentrated

DCM dichloromethane di-t-BPF 1,1'-bis(di-tert-butylphosphino)ferrocene

DMAP 4-dimethylaminopyridine

DMF N,N-dimethylformamide

DSC Differential Scanning Calorimetry

DTBAD di-tert-butyl diazene-1,2-dicarboxylate e.e. enantiomeric excess equiv. equivalents ES electrospray mode HPLC high performance liquid chromatography Inj. Injection IPA Isopropyl alcohol LAH lithium aluminum hydride LCMS liquid chromatography mass spectrometry MS mass spectrometry NaHMDS sodium hexamethyldisilazane NBS N-bromo succinimide NMR nuclear magnetic resonance PE petroleum ether PMB 4-methoxybenzyl RBF round-bottom flask RT room/ambient temperature sat. saturated SFC supercritical fluid chromatography TBAF tetrabutylammonium fluoride TBDPS tert-butyldiphenylsilyl TBDPSCl tert-butylchlorodiphenylsilane TFA trifluoroacetic acid TGA Thermogravimetric analysis THF tetrahydrofuran Tol. toluene UPLC ultra-high performance liquid chromatography wt % weight percent XRPD Powder X-ray Diffraction

Intermediate 1: Methyl 7-bromo-6-chloro-3-(3-methoxy-3-oxopropyl)-1H-indole-2-carboxylate

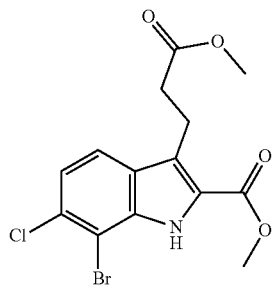

2-Bromo-3-chloroaniline (600 g, 2.91 mol) and concentrated aqueous HCl (1500 mL, 49.4 mol) in water (1500 mL) were placed into a 4-necked RBF. The mixture was stirred overnight to give a solution. A solution of NaNO$_2$ (212 g, 3.07 mol) in water (720 mL) was added dropwise with stirring at 0-5° C. After 1.5 h, a solution of KOAc (4020 g, 40.9 mol) in water (6000 mL) and methyl 2-oxocyclopentane-1-carboxylate (420 g, 2.95 mol) was added dropwise with stirring at 0-5° C. The resulting solution was stirred at 0-5° C. for 0.5 h then for 2 h at RT. The solution was then extracted with 2×10 L of DCM. The combined organic phases were washed with 1×5 L of brine. The solution was dried over anhydrous Na$_2$SO$_4$ and concentrated to yield methyl 1-((2-bromo-3-chlorophenyl)diazenyl)-2-oxocyclopentane-1-carboxylate (1070 g, 100%, 97 wt %).

A solution of conc. sulfuric acid (1000 mL, 18.8 mol) in methanol (10000 mL) and methyl 1-((2-bromo-3-chlorophenyl)diazenyl)-2-oxocyclopentane-1-carboxylate (1400 g, 3.89 mol) were placed into a 4-necked RBF. The resulting solution was stirred at 70° C. in an oil bath for 2 h. The reaction mixture was cooled to 20° C. with a water/ice bath. The solids were collected by filtration. The solid was washed with 2×1 L of MeOH and then dried in an oven under reduced pressure to yield (E/Z)-dimethyl 2-(2-(2-bromo-3-chlorophenyl)hydrazono)hexanedioate (1200 g, 79%).

A solution of conc. sulfuric acid (2 L, 37.5 mol) in methanol (10 L) and (E/Z)-dimethyl 2-(2-(2-bromo-3-chlorophenyl)hydrazono)hexanedioate (1200 g, 2.96 mol, 1.00 equiv) were placed into a 4-necked RBF. The resulting solution was stirred for 72 h at 80° C. in an oil bath. The reaction mixture was cooled to 20° C. with a water/ice bath. The solids were collected by filtration, washed with 1 L of MeOH and then air-dried. The solid was then suspended in 2250 mL of MeOH, with stirring at 50° C. over 30 min. After cooling to 20° C., the solid was collected by filtration and was washed with 500 mL of MeOH and then air-dried to yield methyl 7-bromo-6-chloro-3-(3-methoxy-3-oxopropyl)-1H-indole-2-carboxylate (Intermediate 1, 930 g, 84%); m/z (ES+), [M+H]$^+$=374. $^1$H NMR (400 MHz, CHLOROFORM-d) δ 2.68 (t, 2H), 3.37 (t, 2H), 3.64 (s, 3H), 3.98 (s, 3H), 7.25 (d, 1H), 7.62 (d, 1H), 8.83 (s, 1H).

Intermediate 2: (4-Bromo-1,5-dimethyl-1H-pyrazol-3-yl)methanol

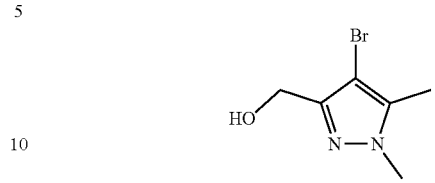

NBS (47.4 g, 266 mmol) was added portionwise over 30 min to a solution of (1,5-dimethyl-1H-pyrazol-3-yl)methanol (32.0 g, 253 mmol) in DCM (500 mL) at 0° C. The resulting mixture was stirred at 25° C. for 1 h. The reaction mixture was diluted with DCM (200 mL), and washed sequentially with water (250 mL) and brine (150 mL). The organic layer was dried over Na$_2$SO$_4$, filtered and concentrated to afford a residue which was washed with PE/EtOAc (1:1) (10 mL) to afford (4-bromo-1,5-dimethyl-1H-pyrazol-3-yl)methanol (Intermediate 2, 48.0 g, 92%), which was used without further purification; m/z (ES+), [M+H]$^+$=205. $^1$H NMR (300 MHz, CHLOROFORM-d) δ 2.08 (s, 1H), 2.26 (s, 3H), 3.79 (s, 3H), 4.63 (s, 2H).

Intermediate 3: 4-Bromo-3-(((4-methoxybenzyl)oxy)methyl)-1,5-dimethyl-1H-pyrazole

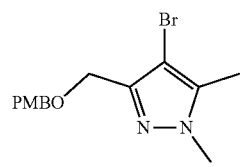

DMF (112 mL) was added to (4-bromo-1,5-dimethyl-1H-pyrazol-3-yl)methanol (Intermediate 2, 3.74 g, 18.3 mmol) and the solution was cooled to 0° C. NaH (0.840 g, 21.0 mmol) (60% in oil) was added. The mixture was stirred at 0° C. for 10 min, allowed to warm to RT and stirred for 20 min, resulting in a white suspension. 1-(Chloromethyl)-4-methoxybenzene (2.72 mL, 20.1 mmol) and KI (0.303 g, 1.83 mmol) were added and the mixture was stirred for 1 h and concentrated to dryness. Water (50 mL) was added and the mixture was extracted with EtOAc (3×20 mL). The combined organic phases were dried over Na$_2$SO$_4$, filtered and concentrated to dryness. The residue was purified by silica gel column chromatography (hexanes/EtOAc) to give 4-bromo-3-(((4-methoxybenzyl)oxy)methyl)-1,5-dimethyl-1H-pyrazole (Intermediate 3, 5.69 g, 96%); m/z (ES+), [M+H]$^+$=325. $^1$H NMR (400 MHz, CHLOROFORM-d) δ 2.26 (s, 3H), 3.80 (s, 3H), 3.81 (s, 3H), 4.47 (s, 2H), 4.53 (s, 2H), 6.85 (d, 2H), 7.33 (d, 2H).

Intermediate 4: 3-(((4-Methoxybenzyl)oxy)methyl)-1,5-dimethyl-4-(4,4,5,5-tetramethyl-1,3,2-dioxaborolan-2-yl)-1H-pyrazole

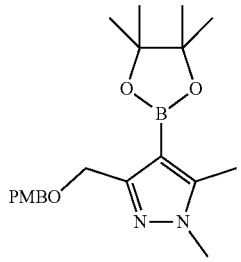

THF (83 mL) was added to 4-bromo-3-(((4-methoxybenzyl)oxy)methyl)-1,5-dimethyl-1H-pyrazole (Intermediate 3, 3.02 g, 9.29 mmol) and the resulting clear solution was cooled to −78° C. Butyllithium (6.96 mL, 11.1 mmol) (1.6 M in hexane) was added at −78° C. under Ar. The mixture was stirred at −78° C. for 50 min. 2-Isopropoxy-4,4,5,5-tetramethyl-1,3,2-dioxaborolane (2.65 mL, 13.0 mmol) was added. The acetone/dry ice bath was removed. The mixture was slowly warmed to RT and was stirred for 4 h. The mixture was concentrated to dryness and EtOAc (200 mL) was added. The resulting suspension was filtered through a pad of diatomaceous earth, washed with EtOAc (50 mL). The filtrate was concentrated to dryness and the residue was purified by silica gel column chromatography (hexanes/EtOAc) to give 3-(((4-methoxybenzyl)oxy)methyl)-1,5-dimethyl-4-(4,4,5,5-tetramethyl-1,3,2-dioxaborolan-2-yl)-1H-pyrazole (Intermediate 4, 2.76 g, 80%); m/z (ES+), [M+H]$^+$=373. $^1$H NMR (400 MHz, CHLOROFORM-d) b 1.28 (s, 12H), 2.40 (s, 3H), 3.76 (s, 3H), 3.80 (s, 3H), 4.57 (s, 2H), 4.61 (s, 2H), 6.86 (d, 2H), 7.33 (d, 2H).

Intermediate 5: 1-((tert-Butyldiphenylsilyl)oxy)propan-2-one

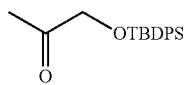

1-Hydroxypropan-2-one (34.9 mL, 463 mmol) was dissolved in anhydrous DMF (150 mL) under Ar. Imidazole (34.1 g, 501 mmol) and DMAP (2.37 g, 19.3 mmol) were added and the solution was cooled to 0° C. TBDPSCl (100 mL, 386 mmol) was added slowly. The mixture was stirred at 0° C. for 15 min, then at RT for 18 h under Ar. Water (1 L) was added and the aqueous phase was extracted with hexanes (4×200 mL). The combined organic phases were washed with brine, dried over Na$_2$SO$_4$, filtered and concentrated to give 1-((tert-butyldiphenylsilyl)oxy)propan-2-one (Intermediate 5, 120 g, 100%). This material was used without further purification; m/z (ES+), [M+18]$^+$=330. $^1$H NMR (400 MHZ, CHLOROFORM-D) b 1.12 (s, 9H), 2.20 (s, 3H), 4.17 (s, 2H), 7.36-7.49 (m, 6H), 7.62-7.70 (m, 4H).

Intermediate 6: Ethyl 5-((tert-butyldiphenylsilyl)oxy)-2-hydroxy-4-oxopent-2-enoate

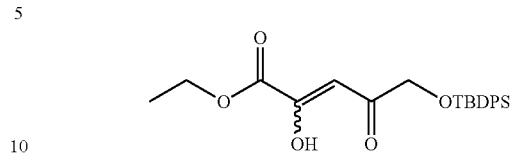

THF (1.50 L) was added to potassium tert-butoxide (69.0 g, 570 mmol) and the solution was cooled to 0° C. Diethyl oxalate (78.1 g, 570 mmol) was added slowly, maintaining the temperature below 0° C. The solution was stirred for 30 min at 0° C. 1-((tert-butyldiphenylsilyl)oxy)propan-2-one (Intermediate 5, 150 g, 480 mmol) was added slowly, maintaining the temperature below 0° C. The reaction mixture was stirred at 0° C. for 1 h, and then EtOAc (300 mL) was added. The resulting mixture was acidified with 1 N HCl to pH=2 to 3. The phases were separated and the aqueous phase was extracted with EtOAc (4×300 mL). The combined organic phases were washed with brine, dried over Na$_2$SO$_4$, filtered and concentrated to dryness to give ethyl 5-((tert-butyldiphenylsilyl)oxy)-2-hydroxy-4-oxopent-2-enoate (Intermediate 6, 160 g, 80%) m/z (ES−), [M−H]$^-$=411. $^1$H NMR (400 MHz, CHLOROFORM-d) b 1.13 (s, 9H), 1.39 (t, 3H), 4.31 (s, 2H), 4.39 (q, 2H), 6.88 (s, 1H) 7.39-7.44 (m, 6H), 7.65-7.68 (m, 4H).

Intermediate 7: Ethyl 5-(((tert-butyldiphenylsilyl)oxy)methyl)-1H-pyrazole-3-carboxylate

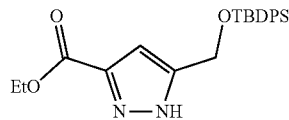

Ethyl 5-((tert-butyldiphenylsilyl)oxy)-2-hydroxy-4-oxopent-2-enoate (Intermediate 6, 350 g, 848 mmol) was dissolved in ethanol (80.5 mL). The solution was cooled to 0° C. and hydrazine monohydrate (53.2 g, 848 mmol, 80 wt %) was added at 0° C. The mixture was stirred at 80° C. for 2 h. After completion, the mixture was cooled to 60° C. and the solvent was removed under reduced pressure. The residue was diluted with EtOAc (161 mL), and washed with saturated NH$_4$Cl (64.6 mL). The aqueous layer was extracted with EtOAc (2×64.6 mL). The combined organic layers were dried over Na$_2$SO$_4$, filtered and evaporated to afford crude product. The crude product was purified by flash silica chromatography (0 to 20% EtOAc in PE) to give ethyl 5-(((tert-butyldiphenylsilyl)oxy)methyl)-1H-pyrazole-3-carboxylate (Intermediate 7, 176 g, 60%); m/z (ES−), [M−H]$^-$=407. $^1$H NMR (400 MHz, DMSO), (reported as a mixture of tautomers) δ 1.00 (s, 9H), 1.28 (t, 3H), 4.28 (q, 2H), 4.73 (d, 2H), 6.54 (s, 1H$_{major}$), 6.71 (s, 1H$_{minor}$), 7.42-7.50 (m, 6H), 7.62-7.65 (m, 4H), 13.48 (s, 1H$_{major}$) 13.81 (s, 1H$_{minor}$).

Intermediate 8: Ethyl 5-(((tert-butyldiphenylsilyl)oxy)methyl)-1-methyl-1H-pyrazole-3-carboxylate

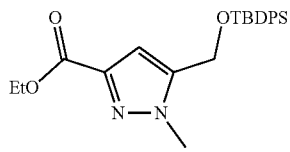

Ethyl 5-(((tert-butyldiphenylsilyl)oxy)methyl)-1H-pyrazole-3-carboxylate (Intermediate 7, 175 g, 428 mmol) was dissolved in anhydrous THF (1750 mL). The solution was cooled to 0° C. and NaHMDS (238 mL, 476 mmol, 2 M in THF) was added at 0° C. The resulting mixture was stirred at 0° C. for 10 min then RT for 30 min. Iodomethane (91.0 g, 642 mmol) was added and the mixture was stirred for 2 h. After completion of reaction, the mixture was concentrated to dryness. EtOAc (3500 mL) was added and the resulting solution was washed with sat. aq. NH$_4$Cl solution (1750 mL). The aqueous phase was extracted with EtOAc (2×3500 mL). The combined organic phases were dried over Na$_2$SO$_4$, filtered and evaporated to afford ethyl 5-(((tert-butyldiphenylsilyl)oxy)methyl)-1-methyl-1H-pyrazole-3-carboxylate (Intermediate 8, 160 g, 88%) which was used without purification; m/z (ES+), [M+H]$^+$=423. $^1$H NMR (300 MHz, CHLOROFORM-d) δ 1.05 (s, 9H), 1.41 (t, 3H), 3.95 (s, 3H), 4.42 (q, 2H), 4.68 (s, 2H), 6.56 (s, 1H), 7.37-7.50 (m, 6H), 7.61-7.69 (m, 4H).

Intermediate 9: (5-(((tert-Butyldiphenylsilyl)oxy)methyl)-1-methyl-1H-pyrazol-3-yl)methanol

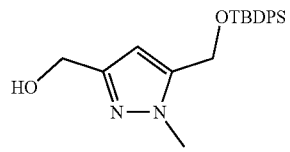

THF (800 mL) was added to ethyl 5-(((tert-butyldiphenylsilyl)oxy)methyl)-1-methyl-1H-pyrazole-3-carboxylate (Intermediate 8, 160 g, 378 mmol) to give an orange solution. The solution was cooled to 0° C. and LAH (189 mL, 47.3 mmol) (2.0 M in THF) was added dropwise, maintaining the temperature below 0° C. The resulting mixture was stirred at 0° C. for 1 h. The mixture was diluted with diethyl ether (1600 mL) and water (14.4 mL) was added dropwise below 0° C., followed by 15% aq. NaOH solution (14.4 mL), and water (43 mL). The resulting mixture was stirred at RT for 10 min. Anhydrous Na$_2$SO$_4$ was added and the suspension was stirred for 15 min. The mass was filtered through a pad of diatomaceous earth and washed with diethyl ether. The filtrate was concentrated to obtain (5-(((tert-butyldiphenylsilyl)oxy)methyl)-1-methyl-1H-pyrazol-3-yl)methanol (Intermediate 9, 140 g, 97%); m/z (ES+), [M+H]$^+$=381. $^1$H NMR (300 MHz, CHLOROFORM-d) δ 1.06 (s, 9H), 3.85 (s, 3H), 4.62 (s, 2H), 4.64 (s, 2H), 6.02 (s, 1H), 7.35-7.53 (m, 6H), 7.62-7.72 (m, 4H).

Intermediate 10: 5-(((tert-Butyldiphenylsilyl)oxy)methyl)-3-(chloromethyl)-1-methyl-1H-pyrazole

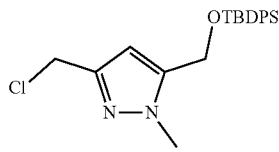

(5-(((tert-butyldiphenylsilyl)oxy)methyl)-1-methyl-1H-pyrazol-3-yl)methanol (Intermediate 9, 380 g, 998 mmol) was dissolved in DCM (4560 mL). The solution was cooled to 0° C. and thionyl chloride (87.4 mL, 1200 mmol) was added very slowly at 0° C. The reaction mixture was allowed to warm to RT and stirred for 1 h. In another flask sat. aq. sodium bicarbonate solution (6330 mL) was cooled to 0° C. The reaction mixture was slowly added to the sodium bicarbonate solution with stirring. The biphasic mixture was stirred until it stopped bubbling. The phases were separated. The organic phase was washed with brine, dried over anhydrous Na$_2$SO$_4$, filtered and concentrated to give 5-(((tert-butyldiphenylsilyl)oxy)methyl)-3-(chloromethyl)-1-methyl-1H-pyrazole (Intermediate 10, 392 g, 98%) m/z (ES+), [M+H]$^+$=399. $^1$H NMR (400 MHz, CHLOROFORM-d) δ 1.05 (s, 9H), 3.83 (s, 3H), 4.55 (s, 2H), 4.64 (s, 2H), 6.05 (s, 1H), 7.34-7.49 (m, 6H), 7.59-7.7 (m, 4H).

Intermediate 11: S-((5-(((tert-Butyldiphenylsilyl)oxy)methyl)-1-methyl-1H-pyrazol-3-yl)methyl)ethanethioate

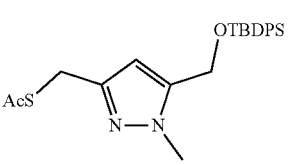

5-(((tert-butyldiphenylsilyl)oxy)methyl)-3-(chloromethyl)-1-methyl-1H-pyrazole (Intermediate 10, 390 g, 977 mmol) was dissolved in acetonitrile (4130 mL). Potassium thioacetate (233 g, 1950 mmol) and sodium iodide (149 g, 9.42 mmol) were added. The reaction mixture was stirred for 12 h. After completion of reaction, the mixture was filtered through a bed of diatomaceous earth and washed with dichloromethane. The filtrate was concentrated under reduced pressure and the residue was purified by silica gel chromatography (0 to 20% EtOAc in hexane) to obtain S-((5-(((tert-butyldiphenylsilyl)oxy)methyl)-1-methyl-1H-pyrazol-3-yl)methyl)ethanethioate (Intermediate 11, 309 g, 72%) m/z (ES+), [M+H]$^+$=439. $^1$H NMR (400 MHz, CHLOROFORM-d) δ 1.04 (s, 9H), 2.34 (s, 3H), 3.80 (s, 3H), 4.08 (s, 2H), 4.60 (s, 2H), 5.92 (s, 1H), 7.35-7.5 (m, 6H), 7.58-7.69 (m, 4H).

Intermediate 12: 3-(Acetylthio)naphthalen-1-yl acetate

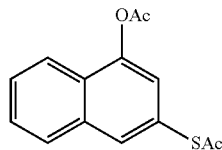

I₂ (38.7 g, 152 mmol) was added in one portion to a mixture of sodium 4-hydroxynaphthalene-2-sulfonate (75.0 g, 305 mmol), Ph₃P (320 g, 1220 mmol) and 18-crown-6 (24.2 g, 91.4 mmol) in toluene (750 mL) at 20° C. under nitrogen. The resulting mixture was stirred at 100° C. for 17 h. 1,4-Dioxane (150 mL) and water (75 mL) were added and the mixture was stirred at 100° C. for a further 1 h. Na₂SO₄ was added. The solids were removed by filtration and the filtrate was partially concentrated under vacuum to afford 3-mercaptonaphthalen-1-ol (360 g, 14 wt % in toluene). The product was used without further purification; m/z (ES⁻), [M−H]⁻=175.

Ac₂O (162 mL, 1720 mmol) was added dropwise to a mixture of DMAP (3.49 g, 28.6 mmol), 3-mercaptonaphthalen-1-ol (360 g, 286 mmol, 14 wt % in toluene) and Et₃N (80 mL, 572 mmol) in DCM (1000 mL) at 0° C. over a period of 10 min under nitrogen. The resulting mixture was stirred at 0° C. for 30 min. The reaction mixture was diluted with DCM (200 mL), and washed sequentially with water (4×750 mL) and saturated brine (500 mL). The organic layer was dried over Na₂SO₄, filtered and concentrated to dryness. The residue was purified by silica gel column chromatography (PE/EtOAc) to give 3-(acetylthio)naphthalen-1-yl acetate (Intermediate 12, 40.0 g, 50% over 2 steps); m/z (ES+), [M+H]+=261. ¹H NMR (400 MHz, CHLOROFORM-d) δ 2.48 (s, 3H), 2.49 (s, 3H), 7.34 (d, 1H), 7.55-7.62 (m, 2H), 7.88-7.92 (m, 3H).

Intermediate 13: Methyl 6-chloro-3-(3-methoxy-3-oxopropyl)-7-(3-(((4-methoxybenzyl)oxy)methyl)-1,5-dimethyl-1H-pyrazol-4-yl)-1H-indole-2-carboxylate

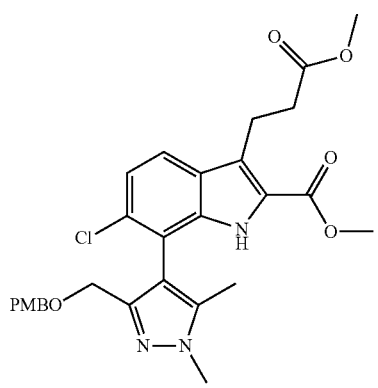

3-((4-methoxybenzyl)oxy)methyl)-1,5-dimethyl-4-(4,4,5,5-tetramethyl-1,3,2-dioxaborolan-2-yl)-1H-pyrazole (Intermediate 4, 18.6 g, 50.1 mmol) was dissolved in a mixture of 1,4-dioxane and water (4:1, 100 mL). Cs₂CO₃ (26.1 g, 80.1 mmol), methyl 7-bromo-6-chloro-3-(3-methoxy-3-oxopropyl)-1H-indole-2-carboxylate (Intermediate 1, 15.0 g, 40.0 mmol) and dichloro[1,1'-bis(di-tert-butylphosphino)ferrocene] palladium(II) (0.783 g, 1.20 mmol) were added, followed by additional dioxane and water (300 mL, 4:1). The mixture was degassed and filled with N₂ three times. The resulting brown clear mixture was placed in an oil bath preheated to 100° C. The mixture was stirred at 100° C. for 3 h. The mixture was cooled to RT and concentrated to 100 mL. EtOAc (200 mL) and water (100 mL) were added. The layers were separated and the aqueous phase was extracted with EtOAc (3×100 mL). The combined organic phases were dried over Na₂SO₄, filtered and concentrated. The residue was purified by silica gel column chromatography (hexanes/EtOAc) to give methyl 6-chloro-3-(3-methoxy-3-oxopropyl)-7-(3-(((4-methoxybenzyl)oxy)methyl)-1,5-dimethyl-1H-pyrazol-4-yl)-1H-indole-2-carboxylate (Intermediate 13, 20.0 g, 92%); m/z (ES+), [M+H]+=540. ¹H NMR (400 MHz, CHLOROFORM-d) δ 2.11 (s, 3H), 2.73 (t, 2H), 3.39-3.50 (m, 2H), 3.68 (s, 3H), 3.75 (s, 3H), 3.78 (s, 3H), 3.91 (s, 3H), 4.14 (d, 1H), 4.33-4.40 (m, 3H), 6.76 (d, 2H), 7.01 (d, 2H), 7.25 (d, 1H), 7.64 (d, 1H), 9.17 (s, 1H).

Intermediate 14: Methyl 6-chloro-3-(3-methoxy-3-oxopropyl)-7-(3-(((4-methoxybenzyl)oxy)methyl)-1,5-dimethyl-1H-pyrazol-4-yl)-1-methyl-1H-indole-2-carboxylate

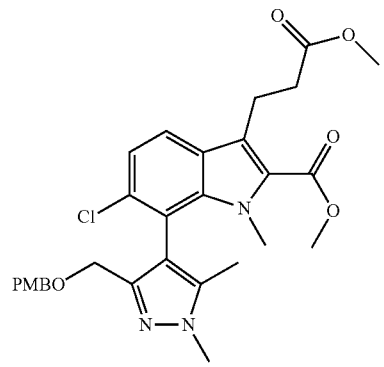

Methyl 6-chloro-3-(3-methoxy-3-oxopropyl)-7-(3-(((4-methoxybenzyl)oxy)methyl)-1,5-dimethyl-1H-pyrazol-4-yl)-1H-indole-2-carboxylate (Intermediate 13, 22.2 g, 37.2 mmol, 90.5 wt %) was dissolved in anhydrous DMF (100 mL). Cs₂CO₃ (18.2 g, 55.8 mmol) was added. The mixture was stirred for 20 min and MeI (4.65 mL, 74.4 mmol) was added. The mixture was stirred for 2.5 h. Water (300 mL) was added and the aqueous phase was extracted with EtOAc (3×100 mL). The combined organic phases were concentrated to dryness. The residue was dissolved in EtOAc (300 mL) and the resulting solution was washed with water (3×50 mL) to further remove DMF. The organic phase was dried over Na₂SO₄, filtered and concentrated to dryness to give methyl 6-chloro-3-(3-methoxy-3-oxopropyl)-7-(3-(((4-methoxybenzyl)oxy)methyl)-1,5-dimethyl-1H-pyrazol-4-yl)-1-methyl-1H-indole-2-carboxylate (Intermediate 14, 22.1 g, 100%, 93.1 wt %), which was used without purification; m/z (ES+), [M+H]+=554. ¹H NMR (400 MHz, CHLOROFORM-d) δ 2.06 (s, 3H), 2.67 (t, 2H), 3.29-3.41 (m, 2H), 3.49 (s, 3H), 3.67 (s, 3H), 3.75 (s, 3H), 3.89 (s, 3H), 3.90 (s, 3H), 4.25-4.36 (m, 4H), 6.67 (d, 2H), 6.86 (d, 2H), 7.23 (d, 1H), 7.62 (d, 1H).

Intermediate 15: Methyl 6-chloro-7-(3-(hydroxymethyl)-1,5-dimethyl-1H-pyrazol-4-yl)-3-(3-methoxy-3-oxopropyl)-1-methyl-1H-indole-2-carboxylate

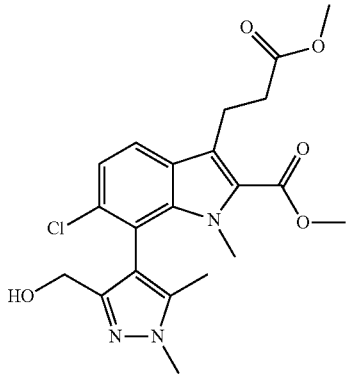 [SMILES: COC(=O)CCc1c(C(=O)OC)n(C)c2c(-c3c(CO)nn(C)c3C)c(Cl)ccc12]

Methyl 6-chloro-3-(3-methoxy-3-oxopropyl)-7-(3-(((4-methoxybenzyl)oxy)methyl)-1,5-dimethyl-1H-pyrazol-4-yl)-1-methyl-1H-indole-2-carboxylate (Intermediate 14, 22.1 g, 37.3 mmol) was dissolved in DCM (56 mL) and TFA (28.7 mL, 373 mmol) was added at 0° C. The ice bath was removed and the mixture was stirred at RT for 1.5 h. DCM (200 mL) was added. The organic phase was washed sequentially with water (3×75 mL) and sat. aq. NaHCO$_3$ (2×50 mL) and the aqueous phase was extracted with DCM (100 mL). The organic phases were combined and 2 mL of MeOH and Et$_3$N (2 mL) were added. The mixture was stirred for 30 min and concentrated to dryness. Water (50 mL) was added and the aqueous phase was extracted with DCM (3×100 mL). The organic phase was dried over Na$_2$SO$_4$, filtered and concentrated. The residue was purified by silica gel column chromatography (DCM/EtOAc then 10% MeOH in DCM) to give methyl 6-chloro-7-(3-(hydroxymethyl)-1,5-dimethyl-1H-pyrazol-4-yl)-3-(3-methoxy-3-oxopropyl)-1-methyl-1H-indole-2-carboxylate (Intermediate 15, 13.7 g, 85%); m/z (ES+), [M+H]$^+$=434. $^1$H NMR (400 MHz, CHLOROFORM-d) δ 2.07 (s, 3H), 2.67 (t, 2H), 3.34 (t, 2H), 3.54 (s, 3H), 3.69 (s, 3H), 3.92 (s, 3H), 3.93 (s, 3H), 4.48 (ABq, 2H), 7.24 (d, 1H), 7.65 (d, 1H).

Intermediate 16: Methyl 6-chloro-7-(3-(chloromethyl)-1,5-dimethyl-1H-pyrazol-4-yl)-3-(3-methoxy-3-oxopropyl)-1-methyl-1H-indole-2-carboxylate

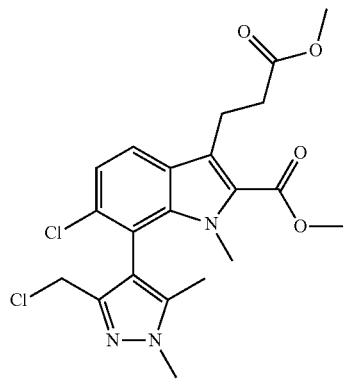 [SMILES: COC(=O)CCc1c(C(=O)OC)n(C)c2c(-c3c(CCl)nn(C)c3C)c(Cl)ccc12]

Methyl 6-chloro-7-(3-(hydroxymethyl)-1,5-dimethyl-1H-pyrazol-4-yl)-3-(3-methoxy-3-oxopropyl)-1-methyl-1H-indole-2-carboxylate (Intermediate 15, 13.0 g, 29.9 mmol) was dissolved in DCM (150 mL) under Ar. The solution was cooled to 0° C. and thionyl chloride (2.62 mL, 35.9 mmol) was added. The ice bath was removed and the mixture was stirred at RT for 30 min, then concentrated. DCM (50 mL) was added and the resulting solution was washed sequentially with sat. aq. NaHCO$_3$ and brine, dried over Na$_2$SO$_4$, filtered and concentrated to give methyl 6-chloro-7-(3-(chloromethyl)-1,5-dimethyl-1H-pyrazol-4-yl)-3-(3-methoxy-3-oxopropyl)-1-methyl-1H-indole-2-carboxylate (Intermediate 16, 13.6 g, 100%) which was used without purification; m/z (ES+), [M+H]$^+$=452. $^1$H NMR (300 MHz, CHLOROFORM-d) δ 2.06 (s, 3H), 2.68 (t, 2H), 3.58 (t, 2H), 3.56 (s, 3H), 3.68 (s, 3H), 3.92 (s, 3H), 3.93 (s, 3H), 4.45 (ABq, 2H), 7.26 (d, 1H), 7.66 (d, 1H).

Intermediate 17: Methyl 6-chloro-7-(3-(iodomethyl)-1,5-dimethyl-1H-pyrazol-4-yl)-3-(3-methoxy-3-oxopropyl)-1-methyl-1H-indole-2-carboxylate

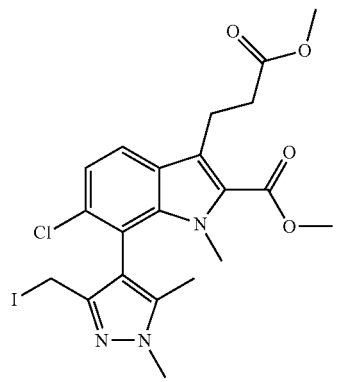 [SMILES: COC(=O)CCc1c(C(=O)OC)n(C)c2c(-c3c(CI)nn(C)c3C)c(Cl)ccc12]

Methyl 6-chloro-7-(3-(chloromethyl)-1,5-dimethyl-1H-pyrazol-4-yl)-3-(3-methoxy-3-oxopropyl)-1-methyl-1H-indole-2-carboxylate (Intermediate 16, 13.5 g, 29.9 mmol) was dissolved in acetonitrile (100 mL) and sodium iodide (7.86 g, 52.4 mmol) was added. The mixture was stirred at 80° C. for 2.5 h. After cooling to RT, the mixture was filtered through a pad of diatomaceous earth and concentrated. Water (100 mL) and EtOAc (100 mL) were added, the layers were separated and the aqueous phase was extracted with EtOAc (2×100 mL). The combined organics were dried over Na$_2$SO$_4$, filtered and concentrated to give methyl 6-chloro-7-(3-(iodomethyl)-1,5-dimethyl-1H-pyrazol-4-yl)-3-(3-methoxy-3-oxopropyl)-1-methyl-1H-indole-2-carboxylate (Intermediate 17, 15.7 g, 96%); m/z (ES+), [M+H]$^+$=544.

$^1$H NMR (400 MHz, CHLOROFORM-d) δ 2.06 (s, 3H), 2.69 (t, 2H), 3.37 (t, 2H), 3.59 (s, 3H), 3.68 (s, 3H), 3.89 (s, 3H), 3.94 (s, 3H), 4.22 (ABq, 2H), 7.27 (d, 1H), 7.68 (d, 1H).

Intermediate 18: Methyl 7-(3-(((((5-((tert-butyldiphenylsilyl)oxy)methyl)-1-methyl-1H-pyrazol-3-yl)methylthio)methyl)-1,5-dimethyl-1H-pyrazol-4-yl)-6-chloro-3-(3-methoxy-3-oxopropyl)-1-methyl-1H-indole-2-carboxylate

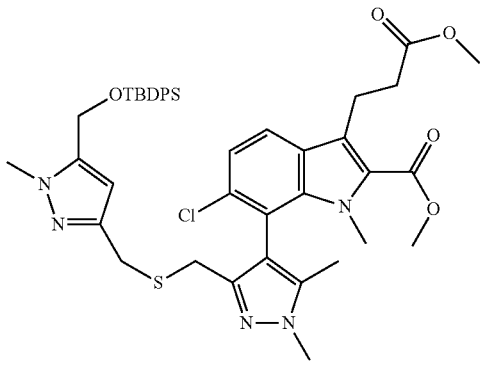

Methyl 6-chloro-7-(3-(iodomethyl)-1,5-dimethyl-1H-pyrazol-4-yl)-3-(3-methoxy-3-oxopropyl)-1-methyl-1H-indole-2-carboxylate (Intermediate 17, 7.60 g, 13.9 mmol) was dissolved in MeOH (30 mL) and THF (15 mL) to give a suspension. K₂CO₃ (1.93 g, 13.9 mmol) was added. The mixture was degassed and filled with N₂. S-((5-(((tert-butyldiphenylsilyl)oxy)methyl)-1-methyl-1H-pyrazol-3-yl)methyl) ethanethioate (Intermediate 11, 6.74 g, 15.4 mmol) in degassed MeOH (15 mL) was added dropwise over 5 min. After addition of the thioacetate solution, the mixture was degassed again, then stirred for 2 h. The mixture was concentrated to dryness and EtOAc (100 mL) was added. The organic phase was washed with water, dried over Na₂SO₄ and concentrated. The residue was purified by silica gel column chromatography (hexanes/EtOAc) to give methyl 7-(3-(((((5-(((tert-butyldiphenylsilyl)oxy)methyl)-1-methyl-1H-pyrazol-3-yl)methyl)thio)methyl)-1,5-dimethyl-1H-pyrazol-4-yl)-6-chloro-3-(3-methoxy-3-oxopropyl)-1-methyl-1H-indole-2-carboxylate (Intermediate 18, 7.10 g, 63%); m/z (ES+), [M+H]⁺=812. ¹H NMR (400 MHz, CHLOROFORM-d) δ 1.04 (s, 9H), 2.04 (s, 3H), 2.65 (t, 2H), 3.32 (t, 2H), 3.52-3.57 (m, 5H), 3.61 (s, 2H), 3.68 (s, 3H), 3.79 (s, 3H), 3.89 (s, 3H), 3.91 (s, 3H), 4.58 (s, 2H), 5.93 (s, 1H), 7.22 (d, 1H), 7.35-7.49 (m, 6H), 7.58 (d, 1H), 7.61-7.71 (m, 4H).

Intermediate 19: Methyl 6-chloro-7-(3-(((((5-(hydroxymethyl)-1-methyl-1H-pyrazol-3-yl)methyl)thio)methyl)-1,5-dimethyl-1H-pyrazol-4-yl)-3-(3-methoxy-3-oxopropyl)-1-methyl-1H-indole-2-carboxylate

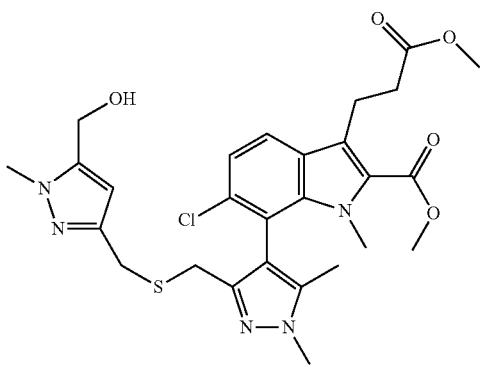

Methyl 7-(3-(((((5-(((tert-butyldiphenylsilyl)oxy)methyl)-1-methyl-1H-pyrazol-3-yl)methyl)thio)methyl)-1,5-dimethyl-1H-pyrazol-4-yl)-6-chloro-3-(3-methoxy-3-oxopropyl)-1-methyl-1H-indole-2-carboxylate (Intermediate 18, 13.9 g, 17.1 mmol) was dissolved in THF (40 mL) and TBAF (17.1 mL, 17.1 mmol) (1 M in THF) was added. The mixture was stirred for 1 h and then concentrated. EtOAc (200 mL) was added and the organic phase was washed sequentially with water and brine, dried over Na₂SO₄, filtered and concentrated. The residue was purified by silica gel column chromatography (hexanes/EtOAc) to give methyl 6-chloro-7-(3-(((((5-(hydroxymethyl)-1-methyl-1H-pyrazol-3-yl)methyl)thio)methyl)-1,5-dimethyl-1H-pyrazol-4-yl)-3-(3-methoxy-3-oxopropyl)-1-methyl-1H-indole-2-carboxylate (Intermediate 19, 8.40 g, 86%); m/z (ES+), [M+H]⁺=574. ¹H NMR (400 MHz, CHLOROFORM-d) δ 2.05 (s, 3H), 2.68 (dd, 2H), 3.35 (dd, 2H), 3.52-3.59 (m, 7H), 3.67 (s, 3H), 3.78 (s, 3H), 3.88 (s, 3H), 3.93 (s, 3H), 4.56 (s, 2H), 5.95 (s, 1H), 7.24 (d, 1H), 7.64 (d, 1H).

Intermediate 20: Methyl 6-chloro-7-(3-(((((5-(chloromethyl)-1-methyl-1H-pyrazol-3-yl)methyl)thio)methyl)-1,5-dimethyl-1H-pyrazol-4-yl)-3-(3-methoxy-3-oxopropyl)-1-methyl-1H-indole-2-carboxylate

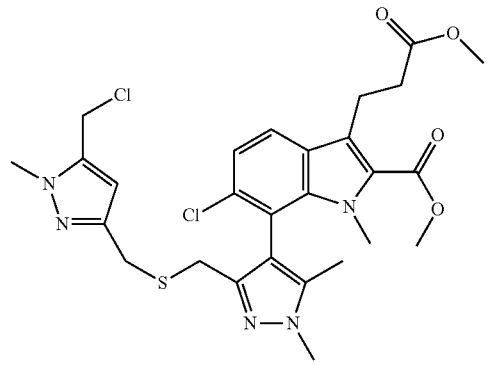

Methyl 6-chloro-7-(3-(((((5-(hydroxymethyl)-1-methyl-1H-pyrazol-3-yl)methyl)thio)methyl)-1,5-dimethyl-1H-pyrazol-4-yl)-3-(3-methoxy-3-oxopropyl)-1-methyl-1H-indole-2-carboxylate (Intermediate 19, 8.70 g, 15.2 mmol) was dissolved in anhydrous DCM (100 mL) under Ar. The mixture was cooled to 0° C. Thionyl chloride (1.33 mL, 18.2 mmol) was added. The ice bath was removed. The mixture was stirred at RT for 30 min and then concentrated. DCM (50 mL) was added. The resulting solution was washed sequentially with water, sat. aq. NaHCO₃ and brine, dried over Na₂SO₄, filtered and concentrated to give methyl 6-chloro-7-(3-(((((5-(chloromethyl)-1-methyl-1H-pyrazol-3-yl)methyl)thio)methyl)-1,5-dimethyl-1H-pyrazol-4-yl)-3-(3-methoxy-3-oxopropyl)-1-methyl-1H-indole-2-carboxylate (Intermediate 20, 9.00 g, 100%), which was used without purification; m/z (ES+), [M+H]⁺=592. ¹H NMR (400 MHz, CHLOROFORM-d) δ 2.05 (s, 3H), 2.65-2.68 (m, 2H), 3.31-3.41 (m, 2H), 3.52-3.59 (m, 7H), 3.68 (s, 3H), 3.79 (s, 3H), 3.89 (s, 3H), 3.93 (s, 3H), 4.49 (s, 2H), 6.07 (s, 1H), 7.25 (d, 1H) 7.63 (d, 1H).

Intermediate 21: Methyl 6-chloro-7-(3-(((((5-(((4-hydroxynaphthalen-2-yl)thio)methyl)-1-methyl-1H-pyrazol-3-yl)methyl)thio)methyl)-1,5-dimethyl-1H-pyrazol-4-yl)-3-(3-methoxy-3-oxopropyl)-1-methyl-1H-indole-2-carboxylate

Intermediate 22: Methyl 6-chloro-7-(3-(((((5-(((4-hydroxynaphthalen-2-yl)thio)methyl)-1-methyl-1H-pyrazol-3-yl)methyl)thio)methyl)-1,5-dimethyl-1H-pyrazol-4-yl)-3-(3-hydroxypropyl)-1-methyl-1H-indole-2-carboxylate

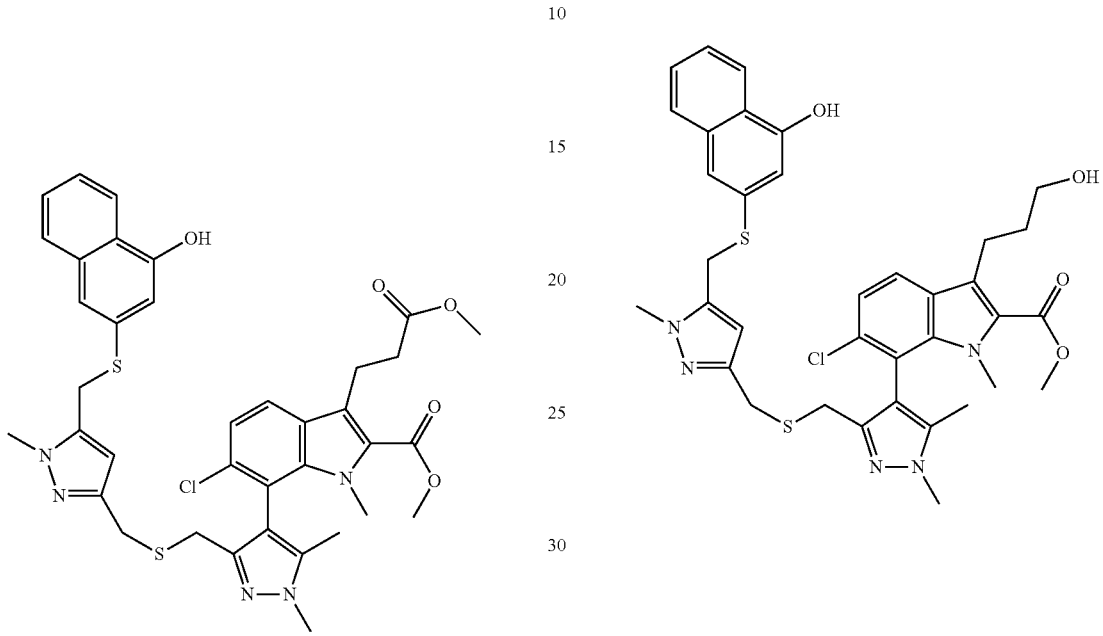

K$_2$CO$_3$ (5.15 g, 37.3 mmol) was added to a mixture of methyl 6-chloro-7-(3-(((((5-(chloromethyl)-1-methyl-1H-pyrazol-3-yl)methyl)thio)methyl)-1,5-dimethyl-1H-pyrazol-4-yl)-3-(3-methoxy-3-oxopropyl)-1-methyl-1H-indole-2-carboxylate (Intermediate 20, 9.20 g, 15.5 mmol) and 3-(acetylthio)naphthalen-1-yl acetate (Intermediate 12, 4.45 g, 17.1 mmol) in MeOH (120 mL). The resulting mixture was stirred for 1 h. The reaction mixture was evaporated to dryness. The residue was redissolved in EtOAc (150 mL). The resulting solution was washed sequentially with water (2×100 mL) and brine (100 mL). The organic layer was dried over Na$_2$SO$_4$, filtered and concentrated. The residue was purified by silica gel column chromatography (0-10% MeOH in DCM) to give methyl 6-chloro-7-(3-(((((5-(((4-hydroxynaphthalen-2-yl)thio)methyl)-1-methyl-1H-pyrazol-3-yl)methyl)thio)methyl)-1,5-dimethyl-1H-pyrazol-4-yl)-3-(3-methoxy-3-oxopropyl)-1-methyl-1H-indole-2-carboxylate (Intermediate 21, 7.42 g, 65.3%); m/z (ES+), [M+H]$^+$=732. $^1$H NMR (300 MHz, CHLOROFORM-d) δ 2.09 (s, 3H), 2.62-2.74 (m, 2H), 3.31-3.66 (m, 12H), 3.70 (s, 3H), 3.94-3.96 (m, 8H), 6.07 (s, 1H), 6.65 (d, 1H) 7.24 (d, 1H), 7.43-7.56 (m, 2H), 7.59-7.71 (m, 2H), 7.71-7.80 (m, 1H), 8.19-8.30 (m, 1H).

Methyl 6-chloro-7-(3-(((((5-(((4-hydroxynaphthalen-2-yl)thio)methyl)-1-methyl-1H-pyrazol-3-yl)methyl)thio)methyl)-1,5-dimethyl-1H-pyrazol-4-yl)-3-(3-methoxy-3-oxopropyl)-1-methyl-1H-indole-2-carboxylate (Intermediate 21, 5.00 g, 6.83 mmol) was dissolved in THF (20 mL) under Ar. The resulting solution was cooled to 0° C. and borane tetrahydrofuran complex (37.6 mL, 37.6 mmol) (1 M in THF) was added. The ice bath was removed and the mixture was stirred at RT for 5.5 h. The reaction mixture was concentrated and cooled to 0° C., followed by addition of MeOH (20 mL) and 6 N HCl (40 mL) (exothermic). The resulting solution was stirred at 0° C. for 10 min, then at RT for 20 min. The volume of the mixture was reduced to ⅓ under reduced pressure. Water (200 mL) was added and the aqueous phase was extracted with 10% MeOH in DCM (9×50 mL). The combined organic phases was washed sequentially with sat. aq. NaHCO$_3$ (50 mL) and brine, dried over Na$_2$SO$_4$, filtered and concentrated. The residue was purified by silica gel column chromatography (hexanes/EtOAc) to give racemic methyl 6-chloro-7-(3-(((((5-(((4-hydroxynaphthalen-2-yl)thio)methyl)-1-methyl-1H-pyrazol-3-yl)methyl)thio)methyl)-1,5-dimethyl-1H-pyrazol-4-yl)-3-(3-hydroxypropyl)-1-methyl-1H-indole-2-carboxylate (Intermediate 22, 4.05 g, 84%); m/z (ES+), [M+H]$^+$=704. $^1$H NMR (400 MHz, CHLOROFORM-d) b 1.93-2.03 (m, 2H), 2.10 (s, 3H), 3.18 (t, 2H), 3.41-3.64 (m, 10H), 3.68 (t, 2H), 3.91-3.98 (m, 8H), 6.05 (s, 1H), 6.64 (d, 1H), 7.25 (d, 1H) 7.43-7.58 (m, 2H), 7.61-7.68 (m, 2H), 7.72-7.81 (m, 1H), 8.26 (d, 1H).

Intermediate 23: Methyl 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylate

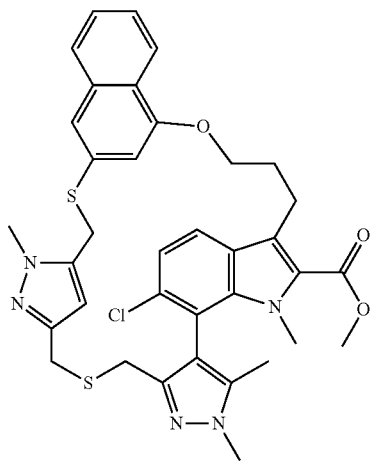 [SMILES: COC(=O)c1c2c3ccc(Cl)c(c3n1C)-c1c(nn(C)c1C)CSCc1cc(n(C)n1)CSc1cc(c3ccccc3c1)OCCC2]

Triphenylphosphine (1.58 g, 6.02 mmol) was dissolved in toluene (30 mL) and a solution of di-tert-butyl diazene-1,2-dicarboxylate (1.39 g, 6.02 mmol) and methyl 6-chloro-7-(3-(((((5-(((4-hydroxynaphthalen-2-yl)thio)methyl)-1-methyl-1H-pyrazol-3-yl)methyl)thio)methyl)-1,5-dimethyl-1H-pyrazol-4-yl)-3-(3-hydroxypropyl)-1-methyl-1H-indole-2-carboxylate (Intermediate 22, 2.12 g, 3.01 mmol) in toluene (27.6 mL) and THF (2.50 mL) was added via addition funnel over 1 h. After addition, the mixture was stirred for 1 h. The reaction mixture was diluted with EtOAc (50 mL) and MeOH (5 mL) and then washed sequentially with water, 2 N HCl and brine, dried over Na$_2$SO$_4$, filtered and concentrated. MeOH (10 mL) was added to the resulting residue. The mixture was sonicated for 5 min to result in a white suspension. The solid was collected, washed with MeOH (6 mL) and dried to give the first batch of product (1.34 g, 64%). The mother liquor was concentrated and the residue was purified by silica gel column chromatography (hexanes/EtOAc) to give the second batch of product. The total amount of methyl 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylate (Intermediate 23) was 1.40 g (68%); m/z (ES+), [M+H]$^+$=686. $^1$H NMR (400 MHz, CHLOROFORM-d) b 2.05 (s, 3H), 2.22-2.25 (m, 1H), 2.38-2.51 (m, 1H), 2.68 (d, 1H), 3.09 (dl H), 3.21-3.32 (m, 2H), 3.45-3.56 (m, 2H), 3.63-3.73 (m, 4H), 3.75-3.84 (m, 4H), 3.84-3.96 (m, 8H), 4.92 (s, 1H), 6.25 (d, 1H), 6.95 (d, 1H), 7.50-7.59 (m, 4H), 7.70-7.81 (m, 1H), 8.22-8.38 (m, 1H).

Intermediate 24 and Intermediate 25: (R$_a$)-(+)-methyl 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylate and (S$_a$)-(−)-methyl 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylate

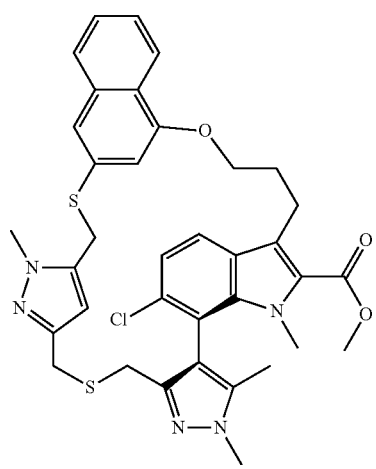

and

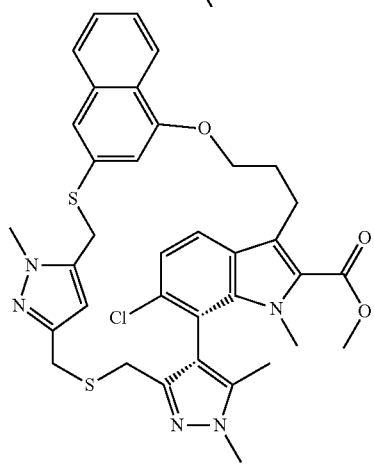

Intermediate 23 (4.70 g, 6.85 mmol) was subjected to chiral SFC (Chiralpak IA® column, 21×250 mm, 5 μm, Temperature=40° C., 45:55 i-PrOH:CO$_2$, UV detection @ 220 nm, loading=150 mg/inj, conc=60 mg/mL, Diluent=MeOH/DCM, flow rate=60 mL/min, Outlet Pressure=100 bar).

Intermediate 24, (R$_a$)-(+)-isomer eluted first (1.87 g, 37%, >98% e.e.): m/z (ES+), [M+H]$^+$=686. $^1$H NMR (400 MHz, CHLOROFORM-d) δ 2.05 (s, 3H), 2.22-2.25 (m, 1H), 2.38-2.51 (m, 1H), 2.67 (d, 1H), 3.09 (d, 1H) 3.19-3.32 (m, 2H), 3.45-3.56 (m, 2H), 3.63-3.73 (m, 4H), 3.75-3.84 (m, 4H), 3.84-3.96 (m, 8H), 4.92 (s, 1H), 6.25 (d, 1H), 6.95 (d, 1H), 7.44-7.59 (m, 4H), 7.70-7.81 (m, 1H), 8.22-8.38 (m, 1H).

Post Purification ee Purity Check:

Chiral analysis method: SFC: Chiralpak IA® column, 4.6×100 mm, 5 μm, Temperature=40° C., 35:65 i-PrOH:

CO$_2$, UV detection at 220 nm, flow rate=5.0 mL/min, Outlet Pressure=125 bar. Retention time of 1.63 min, >98% ee, [α]$_D$+64° (c=0.1, MeOH)

Intermediate 25, (S$_a$)-(−)-isomer eluted second: (1.40 g, 28%, >98% e.e.): m/z (ES+), [M+H]$^+$=686. $^1$H NMR (400 MHz, CHLOROFORM-d) b 2.05 (s, 3H), 2.22-2.25 (m, 1H), 2.38-2.51 (m, 1H), 2.67 (d, 1H), 3.09 (d, 1H) 3.19-3.32 (m, 2H), 3.45-3.56 (m, 2H), 3.63-3.73 (m, 4H), 3.75-3.84 (m, 4H), 3.84-3.96 (m, 8H), 4.92 (s, 1H), 6.25 (d, 1H), 6.95 (d, 1H), 7.44-7.59 (m, 4H), 7.70-7.81 (m, 1H), 8.22-8.38 (m, 1H).

Post Purification ee Purity Check:
Chiral analysis method as for Intermediate 24. Retention time of 3.77 min, >98% ee, [α]$_D$−64° (c=0.1, MeOH)

Example 1: 17-chloro-5,13,14,22-tetramethyl-28-oxa-2,9-dithia-5,6,12,13,22-pentaazaheptacyclo [27.7.1.1$^{4,7}$.0$^{11,15}$.0$^{16,21}$.0$^{20,24}$.0$^{30,35}$]octatriaconta-1 (37),4(38),6,11,14,16,18,20,23,29,31,33,35-tridecaene-23-carboxylic acid

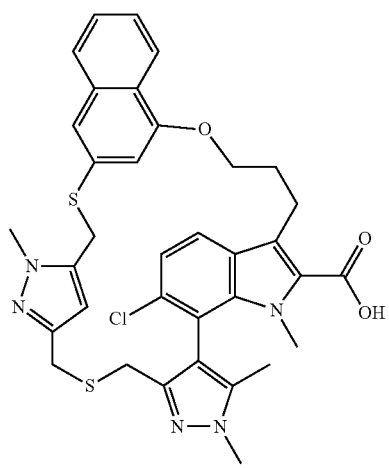 [SMILES: Cc1c2c(nn1C)CSCc1cc(n(C)n1)CSc1cc(c3ccccc3c1)OCCCc1c(C(=O)O)n(C)c3c-2c(Cl)ccc13]

MeOH (48 mL) and THF (48 mL) were added to methyl 17-chloro-5,13,14,22-tetramethyl-28-oxa-2,9-dithia-5,6,12, 13,22 pentaazaheptacyclo[27.7.1.1$^{4,7}$.0$^{11,15}$.0$^{16,21}$ .0$^{20,24}$.0$^{30,35}$]octatriaconta-1(37),4(38),6,11,14,16,18,20,23, 29,31,33,35-tridecaene-23-carboxylate (Intermediate 23, 1.25 g, 1.78 mmol) to result in a suspension. LiOH (0.556 g, 23.2 mmol) and water (12 mL) were added and the suspension was degassed and filled with Ar. The mixture was stirred at 80° C. for 2.5 h. After cooling to RT, 2 N HCl (20 mL) was added and the mixture was concentrated to dryness. Water (50 mL) was added to the residue to result in a white suspension. The white solid was collected by filtration and washed with water (2×10 mL). This solid was redissolved in 10% MeOH in DCM (150 mL), dried over Na$_2$SO$_4$, filtered and concentrated to dryness to give 17-chloro-5,13,14,22-tetramethyl-28-oxa-2,9-dithia-5,6,12, 13,22-pentaazaheptacyclo[27.7.1.1$^{4,7}$.0$^{11,15}$.0$^{16,21}$ .0$^{20,24}$.0$^{30,35}$]octatriaconta-1(37),4(38),6,11,14,16,18,20,23, 29,31,33,35-tridecaene-23-carboxylic acid (Example 1, 1.05 g, 88%); m/z (ES+), [M+H]$^+$=672. $^1$H NMR (400 MHz, DMSO-d6) δ 1.97 (s, 3H), 2.20-2.30 (m, 1H), 2.35-2.50 (m, 1H), 2.90 (d, 1H), 3.07-3.19 (m, 3H), 3.40-3.47 (m, 2H), 3.50 (s, 3H), 3.71 (s, 3H), 3.76 (s, 3H), 3.86 (dd, 1H), 4.07-4.15 (m, 1H), 4.27 (s, 2H), 4.76 (s, 1H), 6.67 (s, 1H), 7.14 (d, 1H), 7.39 (s, 1H), 7.45-7.52 (m, 2H), 7.71 (d, 1H), 7.87 (d, 1H), 8.10 (d, 1H), 13.32 (br. s., 1H).

Example 2: (R$_a$)-(+)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid

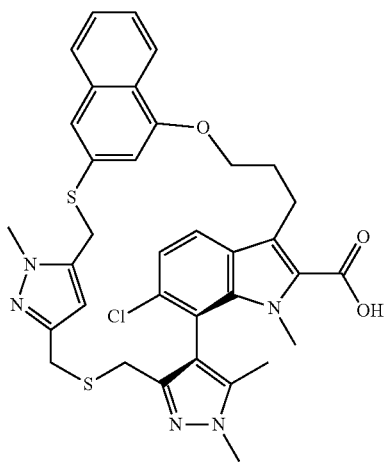

(R$_a$)-(+)-methyl 17-chloro-5,13,14,22-tetramethyl-28-oxa-2,9-dithia-5,6,12,13,22-pentaazaheptacyclo[27.7.1. 1$^{4,7}$.0$^{11,15}$.0$^{16,21}$.0$^{20,24}$.0$^{30,35}$]octatriaconta 1(37),4(38),6,11, 14,16,18,20,23,29,31,33,35-tridecaene-23-carboxylate (Intermediate 24, 1.87 g, 2.51 mmol) was dissolved in MeOH (8.35 mL), THF (8.35 mL) and water (8.35 mL). LiOH (0.90 g, 37.6 mmol) was added. The mixture was stirred for 4 h. The mixture was concentrated to dryness. 2 N HCl (25 mL) was added. The aqueous phase was extracted with 5% MeOH in DCM (4×30 mL). The combined organic phases were washed with brine, dried over Na$_2$SO$_4$, filtered and concentrated. MeOH (20 mL) was added to the residue to result in a clear solution. This clear solution was concentrated to give a white solid which was dried under vacuum to give (R$_a$)-(+)-17-chloro-5,13,14,22-tetramethyl-28-oxa-2,9-dithia-5,6,12,13,22-pentaazaheptacyclo[27.7.1.1$^{4,7}$ .0$^{11,15}$.0$^{16,21}$.0$^{20,24}$.0$^{30,35}$]octatriaconta-1(37),4(38),6,11,14, 16,18,20,23,29,31,33,35-tridecaene-23-carboxylic acid (Example 2, 1.55 g, 92%, >98% e.e.); m/z (ES+), [M+H]$^+$=672. $^1$H NMR (400 MHz, DMSO-d6) b 1.97 (s, 3H), 2.20-2.30 (m, 1H), 2.35-2.50 (m, 1H), 2.90 (d, 1H), 3.07-3.19 (m, 3H), 3.40-3.47 (m, 2H), 3.50 (s, 3H), 3.71 (s, 3H), 3.76 (s, 3H), 3.86 (dd, 1H), 4.07-4.15 (m, 1H), 4.26 (s, 2H), 4.75 (s, 1H), 6.67 (s, 1H), 7.14 (d, 1H), 7.38 (s, 1H), 7.45-7.52 (m, 2H), 7.71 (d, 1H), 7.87 (d, 1H), 8.10 (d, 1H), 13.32 (br. s. 1H).

Post Purification ee Purity Check:
Chiral analysis method: SFC: Chiralpak ID® column, 4.6×250 mm, 5 μm, Temperature=40° C., 40:60 MeOH: CO$_2$, UV detection at 220 nm, flow rate=2.8 mL/min, Outlet Pressure=100 bar, retention time of 7.33 min, >98% e.e., [α]$_D$+87° (C=0.042, MeOH)

Example 3: $(S_a)$-(−)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid

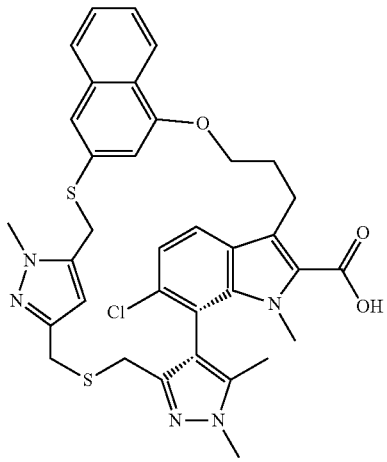

Starting from $(S_a)$-(−)-methyl 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta 1(37), 4(38),6,11,14,16,18,20,23,29,31,33,35-tridecaene-23-carboxylate (Intermediate 25, 1.40 g, 2.04 mmol), the same procedure given for Example 2 was performed to obtain $(S_a)$-(−)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Example 3, 1.25 g, 91%, >98% e.e.); m/z (ES+), [M+H]$^+$=672. $^1$H NMR (400 MHz, DMSO-d6) δ 1.97 (s, 3H), 2.20-2.30 (m, 1H), 2.35-2.50 (m, 1H), 2.90 (d, 1H), 3.07-3.19 (m, 3H), 3.40-3.47 (m, 2H), 3.50 (s, 3H), 3.71 (s, 3H), 3.76 (s, 3H), 3.86 (dd, 1H), 4.07-4.15 (m, 1H), 4.27 (s, 2H), 4.76 (s, 1H), 6.67 (s, 1H), 7.14 (d, 1H), 7.38 (s, 1H), 7.45-7.52 (m, 2H), 7.71 (d, 1H), 7.87 (d, 1H), 8.10 (d, 1H), 13.32 (br. s., 1H).

Post Purification ee Purity Check:

Chiral analysis method as for Example 2: Retention time of 9.36 min, >98% e.e., $[\alpha]_D$ −92° (c=0.048

Example 4: In Vitro Activity of Example 1, 2, and 3

Caspase Activity Assay

This is a cell assay to measure the induction of apoptosis in MOLP-8 (multiple myeloma), KMS-12-BM (multiple myeloma), MV-4-11 (acute myeloid leukemia), and NCI-H23 (non-small cell lung cancer) cells after 6 h treatment. On the first day, 3000 (MOLP-8, KMS-12-BM, MV-4-11) or 1250 (NCI-H23) cells/well were seeded in 50 µL of growth media (IMDM+10% FBS+2 mM L-Glu for MV-4-11 and RPMI-1640+10% FBS+2 mM L-Glu for all other cell lines) in 384-well white microplates, and incubated overnight (37° C., 5% $CO_2$, 80% RH). On the second day, the cells were treated with Mcl-1 inhibitors using an ECHO acoustic liquid handler (10 point half-log serial dilution, 31.5 µM top concentration, 0.3% final DMSO concentration). After 6 h incubation (37° C., 5% $CO_2$, 80% RH), 25 µL of Caspase-Glo 3/7 reagent (Promega) was added into each well, and plates were incubated at room temperature for 30 min protected from light. Luminescence was recorded using an Infinite M200 microplate reader (Tecan) with a 100 ms integration time. $EC_{50}$ values were calculated using GeneData analysis software.

TABLE 1

Results from in vitro Caspase Activity assay

| Cell Line | Example 1 (Compound I) Caspase Activity, $EC_{50}$ (nM) | Example 2 (Compound II) Caspase Activity, $EC_{50}$ (nM) | Example 3 (Compound III) Caspase Activity, $EC_{50}$ (nM) |
|---|---|---|---|
| MOLP-8 | 44 | 30 | >2300 |
| KMS-12-BM | 48 | 43 | >1030 |
| MV-4-11 | 24 | 20 | >1580 |
| NCI-H23 | 531 | 193 | >10000 |

Example 5: Solid forms of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid X-Ray Powder Diffraction (XRPD) Analysis XRPD analysis was performed using a Bruker D4 diffractometer, which is commercially available from Bruker AXS Inc™ (Madison, Wis.). The XRPD spectra were obtained by mounting a sample (approximately 20 mg) of the material for analysis on a single silicon crystal wafer mount (e.g., a Bruker silicon zero background X-ray diffraction sample holder) and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms (i.e., about 1.54 angstroms). The sample was exposed for 1 second per 0.02 degree 2-theta increment (continuous scan mode) over the range 2 degrees to 40 degrees 2-theta in theta-theta mode. The running time was 31 min, 41 s.

XRPD 2θ values may vary with a reasonable range, e.g., in the range ±0.2° and that XRPD intensities may vary when measured for essentially the same crystalline form for a variety of reasons including, for example, preferred orientation. Principles of XRPD are described in publications, such as, for example, Giacovazzo, C. et al. (1995), Fundamentals of Crystallography, Oxford University Press; Jenkins, R. and Snyder, R. L. (1996), Introduction to X-Ray Powder Diffractometry, John Wiley & Sons, New York; and Klug, H. P. & Alexander, L. E. (1974), X-ray Diffraction Procedures, John Wiley and Sons, New York.

DSC Analysis

DSC analysis was performed on samples prepared according to standard methods using a Q SERIES™ Q1000 DSC calorimeter available from TA INSTRUMENTS® (New Castle, Del.). A sample (approximately 2 mg) was weighed into an aluminum sample pan and transferred to the DSC. The instrument was purged with nitrogen at 50 mL/min and data collected between about 22° C. and 300° C., using a dynamic heating rate of about 10° C./minute. Thermal data was analyzed using standard software, e.g., Universal v.4.5A from TA INSTRUMENTS®.

Thermogravimetry Analysis (TGA)

TGA was performed on samples prepared according to standard methods using a Q SERIES™ Q5000 thermogravimetry analyzer available from TA Instruments INSTRUMENTS® (New Castle, Del.). A sample (approximately 5 mg) was placed into an aluminum sample pan and transferred to the TGA furnace. The instrument was purged with nitrogen at 50 mL/min and data collected between 25° C. and 300° C., using a dynamic heating rate of 10° C./minute. Thermal data was analyzed using standard software, e.g., Universal v.4.5A from TA INSTRUMENTS®.

Preparation of Form A ($R_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate Method 1:

10 mg of ($R_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid was dissolved in 1.0 mL of MeOH and 5 drops of water. The resulting solution was evaporated in ambient conditions to dryness. The resulting white powder was identified as Form A.

Method 2:

10 mg of ($R_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid Form C (or Form F) was suspended in 0.2 mL of water. The resulting slurry was stirred for 2 days. The resulting solid was identified as Form A.

Method 3:

An amount of 1.5 g of ($R_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Form F) was added to a vessel and 4.5 mL of MeOH and 0.5 mL of H$_2$O (9:1) were added to obtain a suspension. The resulting slurry was stirred overnight and the slurry was evaporated to dryness. XRPD showed that Form F converted to Form A.

Form A (Method 3) was analyzed by XRPD and the results are tabulated below (Table 2) and shown in FIG. 1.

TABLE 2

| XRPD Peaks for Form A | |
|---|---|
| Angle (2θ ± 0.2°) | Intensity (%) |
| 18.2 | 100.0 |
| 12.5 | 87.7 |
| 14.4 | 82.7 |
| 8.4 | 75.8 |
| 17.2 | 70.4 |
| 26.8 | 64.4 |
| 10.7 | 59.0 |
| 27.7 | 55.9 |
| 30.2 | 45.6 |
| 23.0 | 42.0 |
| 20.5 | 40.5 |
| 19.2 | 39.4 |
| 7.0 | 35.9 |
| 25.0 | 35.3 |
| 17.6 | 34.5 |

TABLE 2-continued

| XRPD Peaks for Form A | |
|---|---|
| Angle (2θ ± 0.2°) | Intensity (%) |
| 23.7 | 34.4 |
| 19.8 | 33.4 |
| 24.5 | 31.8 |
| 22.0 | 30.9 |
| 20.9 | 30.8 |
| 24.2 | 28.8 |
| 37.6 | 27.1 |
| 31.5 | 26.9 |
| 22.3 | 26.5 |
| 13.9 | 25.3 |
| 13.7 | 23.9 |
| 29.0 | 23.9 |
| 34.5 | 22.9 |
| 26.3 | 21.3 |
| 13.1 | 20.8 |
| 29.4 | 20.7 |
| 15.6 | 19.8 |
| 36.9 | 17.9 |
| 15.1 | 17.9 |
| 36.4 | 16.7 |
| 32.8 | 16.6 |
| 38.2 | 16.2 |
| 28.6 | 16.1 |
| 35.5 | 14.9 |

Form A (Method 3) was analyzed by thermal techniques. DSC analysis indicated that Form A has an endotherm event of desolvation with an onset at about 121° C. and a peak at about 158° C., followed by an endotherm event of melting/decomposition with an onset at about 181° C. and a peak at about 194° C. TGA indicated that Form A exhibits a mass loss of about 4.0% upon heating from about 25° C. to about 160° C. A representative DSC/TGA thermogram of Form A is shown in FIG. 2.

Single crystals of Form A were obtained from slow evaporation of a MeOH/H$_2$O (1:1 volume ratio). Single crystal structure analysis confirmed that Form A is a monohydrate form. Crystallographic data: Space group monoclinic P2(1), unit cell dimensions: a=13.83(3) Å, b=7.578 (14) Å, c=33.57(6) Å, β=90.23(2)°, V=3518(12) Å$^3$.

Preparation of Form B ($R_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid Single crystals of ($R_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid Form B were obtained from slow evaporation of a MeOH solution of ($R_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid with 1:1 mole ratio of meglumine. As crystals appeared from the solution, one was manually collected. Single crystal structure analysis confirmed that Form B is a mono-methanolic solvate of the free acid. Crystallographic data: Space group Orthorhombic P2(1)2(1)2(1), unit cell dimensions: a=7.530(7) Å, b=13.956(12) Å, c=34.44(3) Å, V=3619(5) Å3.

Preparation of Form C(R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid Method 1:
300 mg of amorphous (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid was taken up in EtOH (3 mL) and heated to dissolve. After cooling to RT, the solution was stirred overnight, whereupon a solid had precipitated. This was collected by filtration and dried to yield Form C (266 mg, 81%).

Method 2:
10 mg of amorphous (R$_a$)-17-chloro-5,13,14,22-tetramethyl-28-oxa-2,9-dithia-5,6,12,13,22-pentaazaheptacyclo[27.7.1.1$^{47}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid was suspended in 0.2 mL of EtOH. The resulting slurry was stirred for 1 day. Form C was obtained after evaporation of the slurry in ambient conditions. Form C (Method 1) was analyzed by XRPD and the results are tabulated below (Table 3) and shown in FIG. 3.

TABLE 3

XRPD Peaks for Form C

| Angle (2θ ± 0.2°) | Intensity (%) |
|---|---|
| 10.2 | 100.0 |
| 5.1 | 87.4 |
| 8.1 | 41.2 |
| 25.5 | 33.5 |
| 12.0 | 26.9 |
| 28.9 | 26.0 |
| 18.9 | 25.4 |
| 18.0 | 25.0 |
| 20.4 | 22.3 |
| 14.2 | 17.6 |
| 16.5 | 17.4 |
| 21.5 | 13.8 |
| 14.8 | 12.9 |
| 22.3 | 12.8 |
| 15.3 | 12.2 |

Form C (Method 1) was analyzed by thermal techniques. DSC analysis indicated that Form C has an endotherm event of desolvation with an onset at about 123° C. and a peak at about 140° C., followed by an endotherm event of melting/decomposition with an onset at about 185° C. and a peak at about 196° C. TGA indicated that Form C exhibits a mass loss of about 6.4% upon heating from about 25° C. to about 160° C. A representative DSC/TGA thermogram of Form C is shown in FIG. 4.

Preparation of Form D (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid Method 1:
10 mg of amorphous (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid was suspended in 0.2 mL of EtOAc. The resulting slurry was stirred for 1 day and a partial crystalline material was obtained. The external temperature of the vial was heated to 100° C. and the resulting slurry stirred for 15 minutes. The slurry was stirred for 3 days after cooling down to ambient temperature and Form D was identified.

Method 2:
10 mg of amorphous (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid was dissolved in 0.2 mL hot acetone, and the white solid was precipitated after the clear solution was cooled down to the room temperature. The resulting suspension was stirred for 3 days. Form D was identified.

Form D (Method 2) was analyzed by XRPD and the results are tabulated below (Table 4) and are shown in FIG. 5.

TABLE 4

XRPD Peaks for Form D

| Angle (2θ ± 0.2°) | Intensity (%) |
|---|---|
| 5.7 | 100.0 |
| 5.6 | 96.3 |
| 19.5 | 70.5 |
| 8.0 | 65.5 |
| 21.9 | 53.5 |
| 14.8 | 40.7 |
| 16.5 | 36.5 |
| 18.5 | 35.7 |
| 11.7 | 31.9 |
| 13.4 | 31.9 |

Form D (Method 2) was analyzed by thermal techniques. DSC analysis indicated that Form D has an endotherm event of melting with an onset at about 156° C. and a peak at about 175° C. TGA indicated that Form D exhibits a mass loss of about 3.6% upon heating from about 25° C. to about 170° C. A representative DSC/TGA thermogram of Form D is shown in FIG. 6.

Preparation of Form E (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid 5 mg of (R$_a$)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid was dissolved in 0.5 mL hot IPA/H$_2$O (3:1) and crystals were obtained after the solution was cooled. The solution was slowly evaporated to dryness. Form E was identified.

Form E was analyzed by XRPD and the results are tabulated below (Table 5) and are shown in FIG. 7.

TABLE 5

XRPD Peaks for Form E

| Angle (2θ ± 0.2°) | Intensity (%) |
|---|---|
| 8.3 | 100.0 |
| 10.2 | 78.4 |
| 17.5 | 72.1 |
| 18.6 | 68.6 |

TABLE 5-continued

XRPD Peaks for Form E

| Angle (2θ ± 0.2°) | Intensity (%) |
|---|---|
| 22.1 | 50.2 |
| 23.3 | 43.1 |
| 27.4 | 41.4 |
| 20.4 | 40.5 |
| 16.0 | 37.9 |
| 33.7 | 37.6 |
| 36.9 | 36.5 |
| 16.5 | 36.1 |
| 11.6 | 35.6 |
| 31.9 | 33.9 |
| 21.6 | 33.9 |
| 19.6 | 33.8 |
| 26.6 | 33.0 |
| 12.6 | 31.9 |
| 14.9 | 30.1 |
| 25.0 | 29.3 |
| 13.9 | 25.9 |

Preparation of Form F $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid pentahydrate 5 mg of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid was dissolved in 1.0 mL of EtOH/H$_2$O (3:1), and the resulting solution was slowly evaporated in the hood. The resulting crystalline material was identified as Form F.

Form F was analyzed by XRPD and the results are tabulated below (Table 6) and are shown in FIG. 8.

TABLE 6

XRPD Peaks for Form F

| Angle (2θ ± 0.2°) | Intensity (%) |
|---|---|
| 5.3 | 100.0 |
| 7.9 | 88.3 |
| 10.6 | 75.3 |
| 18.9 | 69.6 |
| 14.3 | 64.0 |
| 26.8 | 60.8 |
| 21.7 | 60.8 |
| 24.7 | 60.7 |
| 16.7 | 57.9 |
| 24.3 | 55.9 |
| 21.5 | 53.5 |
| 11.9 | 53.5 |
| 22.8 | 46.5 |
| 17.1 | 44.3 |
| 19.6 | 44.2 |
| 14.9 | 39.3 |
| 15.7 | 38.6 |
| 20.5 | 36.7 |
| 28.2 | 36.3 |
| 33.6 | 34.6 |
| 23.6 | 30.8 |
| 31.1 | 30.0 |

Form F was analyzed by thermal techniques. DSC analysis indicated that Form F has an endotherm event of desolvation with an onset at about 40° C. and a peak at about 67° C., followed by an endotherm event of melting/decomposition with an onset at about 185° C. and a peak at about 195° C. TGA indicated that Form F exhibits a mass loss of about 4.3% upon heating from about 25° C. to about 100° C. A representative DSC/TGA thermogram for Form F is shown in FIG. 9.

10 mg of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid was dissolved in 1.0 mL of Acetone/H$_2$O (4:1), and the resulting solution was slowly evaporated to dryness to yield Form F. Single crystal structure analysis showed that it is a pentahydrate form. Crystallographic data: Space group Triclinic P1, unit cell dimensions: a=7.458(9) Å, b=13.993(17) Å, c=16.90(2) Å, α=96.298(15)°, β=91.987(13)°, γ=91.604(14)°, and V=1751(4) Å$^3$.

Preparation of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, sodium salt 135 mg of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid Form C (0.2 mmol) was suspended in 5 mL of MeOH, and to the suspension 200 μL of 1.0 N NaOH aqueous solution is added. The slurry was stirred until the solid dissolved. The clear solution was evaporated, and the resulting solid was slurried with EtOAc for 3 days. A crystalline material was obtained after the slurry was evaporated to dryness.

The crystals were analyzed by XRPD and the results are tabulated below (Table 7) and shown in FIG. 10.

TABLE 7

XRPD Peaks for Sodium Salt

| Angle (2θ ± 0.2°) | Intensity (%) |
|---|---|
| 10.7 | 100.0 |
| 18.0 | 85.9 |
| 19.3 | 85.4 |
| 11.5 | 78.0 |
| 18.6 | 68.5 |
| 19.9 | 64.4 |
| 26.6 | 62.5 |
| 23.2 | 60.1 |
| 16.3 | 59.7 |
| 29.4 | 47.3 |
| 27.0 | 46.1 |
| 25.8 | 45.6 |
| 13.4 | 41.0 |

TABLE 7-continued

XRPD Peaks for Sodium Salt

| Angle (2θ ± 0.2°) | Intensity (%) |
|---|---|
| 30.1 | 40.4 |
| 28.1 | 40.4 |
| 30.6 | 40.1 |
| 22.2 | 38.2 |
| 25.3 | 35.6 |
| 21.8 | 29.9 |
| 24.2 | 28.6 |

The sodium salt was analyzed by thermal techniques. DSC analysis indicated that the sodium salt has a broad endotherm event of desolvation from about 100° C. to about 200° C., followed by an endotherm event of melting with an onset at about 239° C. and a peak at about 246° C. TGA indicated that the sodium salt exhibits a mass loss of about 4.0% upon heating from about 25° C. to about 175° C. A representative DSC/TGA thermogram of the sodium salt is shown in FIG. 11.

Preparation of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid, meglumine salt 135 mg of $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (0.2 mmol) was suspended in 2 mL of MeOH and 4 mL of 0.05 M meglumine solution in MeOH was added. The slurry was stirred overnight and then evaporated to dryness. About 2 mL of EtOAc was added to yield a slurry, and the slurry was stirred for 3 days. Crystalline material was obtained after the slurry was evaporated to dryness.

The meglumine salt was analyzed by XRPD and the results are tabulated below (Table 8) and shown in FIG. 12.

TABLE 8

XRPD Peaks for Meglumine Salt

| Angle (2θ ± 0.2°) | Intensity (%) |
|---|---|
| 6.3 | 100.0 |
| 6.6 | 87.2 |
| 7.6 | 73.5 |
| 18.2 | 57.5 |
| 8.5 | 49.7 |
| 18.8 | 37.6 |
| 21.8 | 28.4 |
| 12.9 | 28.3 |
| 16.2 | 28.1 |
| 11.8 | 26.9 |
| 23.8 | 25.9 |
| 19.9 | 23.6 |
| 22.7 | 23.4 |
| 27.4 | 22.1 |
| 14.3 | 20.8 |
| 25.2 | 19.1 |
| 15.7 | 18.1 |

The meglumine salt was analyzed by thermal techniques. DSC analysis indicated that the meglumine salt has a broad endotherm event of desolvation with an onset at about 69° C. and a peak at about 88° C., followed by an endotherm event of desolvation with an onset at about 102° C. and a peak at about 104° C. TGA indicated that the meglumine salt exhibits a mass loss of about 10.6% upon heating from about 25° C. to about 150° C. A representative DSC/TGA thermogram of the meglumine salt is shown in FIG. 13.

Example 6: Single Agent and Combination Activity of Example 2 In Vivo in Human Multiple Myeloma Tumor Models Method: Example 2 was formulated in 30% 2-Hydroxypropyl-beta-cyclodextrin (HPBCD), pH 9 and dosed as intravenously (iv) in a volume of 5 ml/kg. 5×10$^6$ MOLP-8 tumor cells or 10$^7$ NCI-H929 tumor cells were injected subcutaneously in the right flank of C.B-17 SCID female mice in a volume of 0.1 mL. Tumor volumes (measured by caliper) were calculated using the formula: length (mm)× width (mm)$^2$/0.52. For efficacy studies, mice were randomized based on tumor volumes and growth inhibition was assessed by comparison of the differences in tumor volume between control and treated groups. Dosing began when mean tumor size reached approximately 160 mm$^3$ for MOLP-8 and approximately 230 mm$^3$ for NCI-H929.

Figure 14:
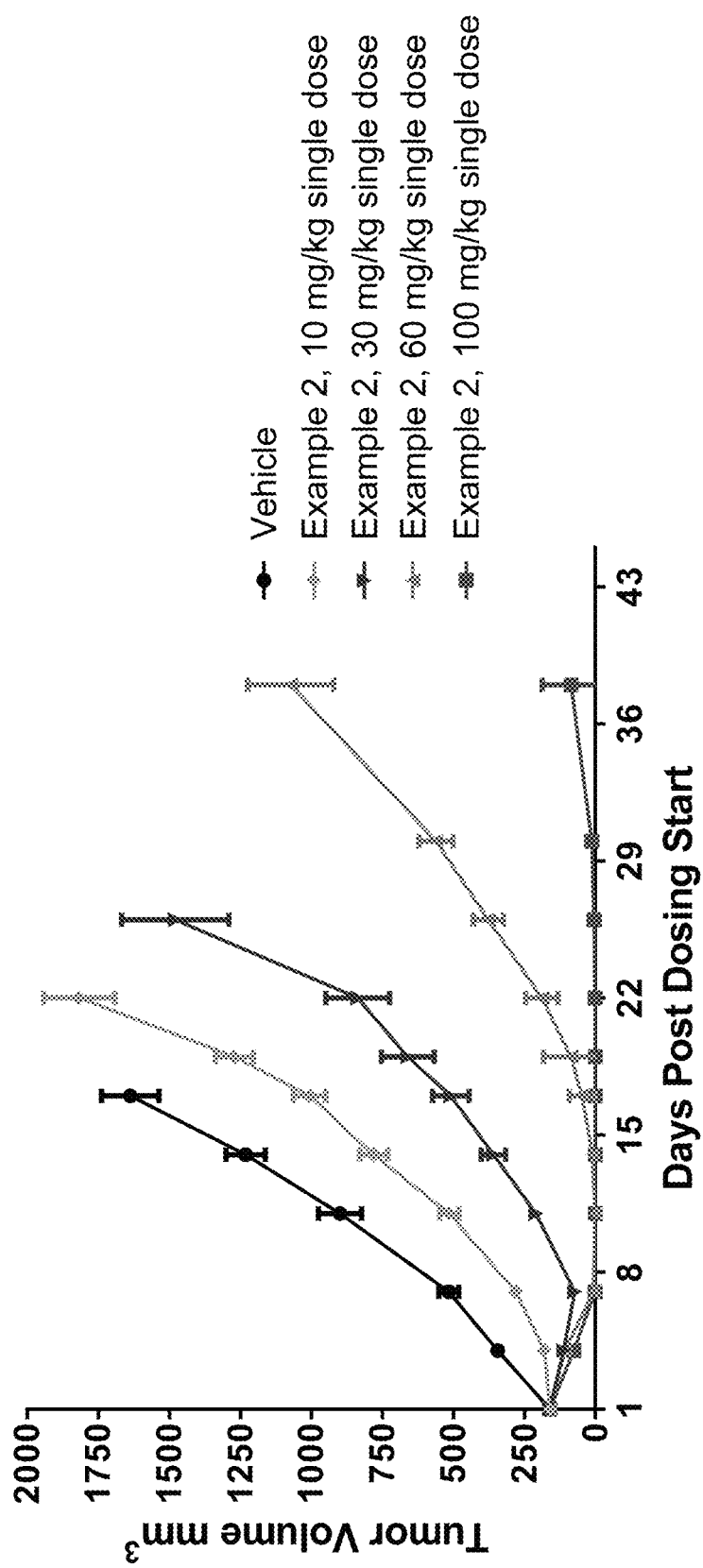
FIG. 14 illustrates the dose dependent anti-tumor activity of Example 2 in MOLP-8 tumor bearing mice.

Results:

Example 2 induced dose dependent anti-tumor activity in MOLP-8 tumor bearing mice (FIG. 14). A single iv administration of Example 2 at 10 or 30 mg/kg resulted in significant anti-tumor activity of 52% and 92% tumor growth inhibition (TGI), respectively. A single iv administration of Example 2 at 60 or 100 mg/kg induced complete tumor regression in 13 out of 14 mice measured 10 days after dosing.

Figure 15:
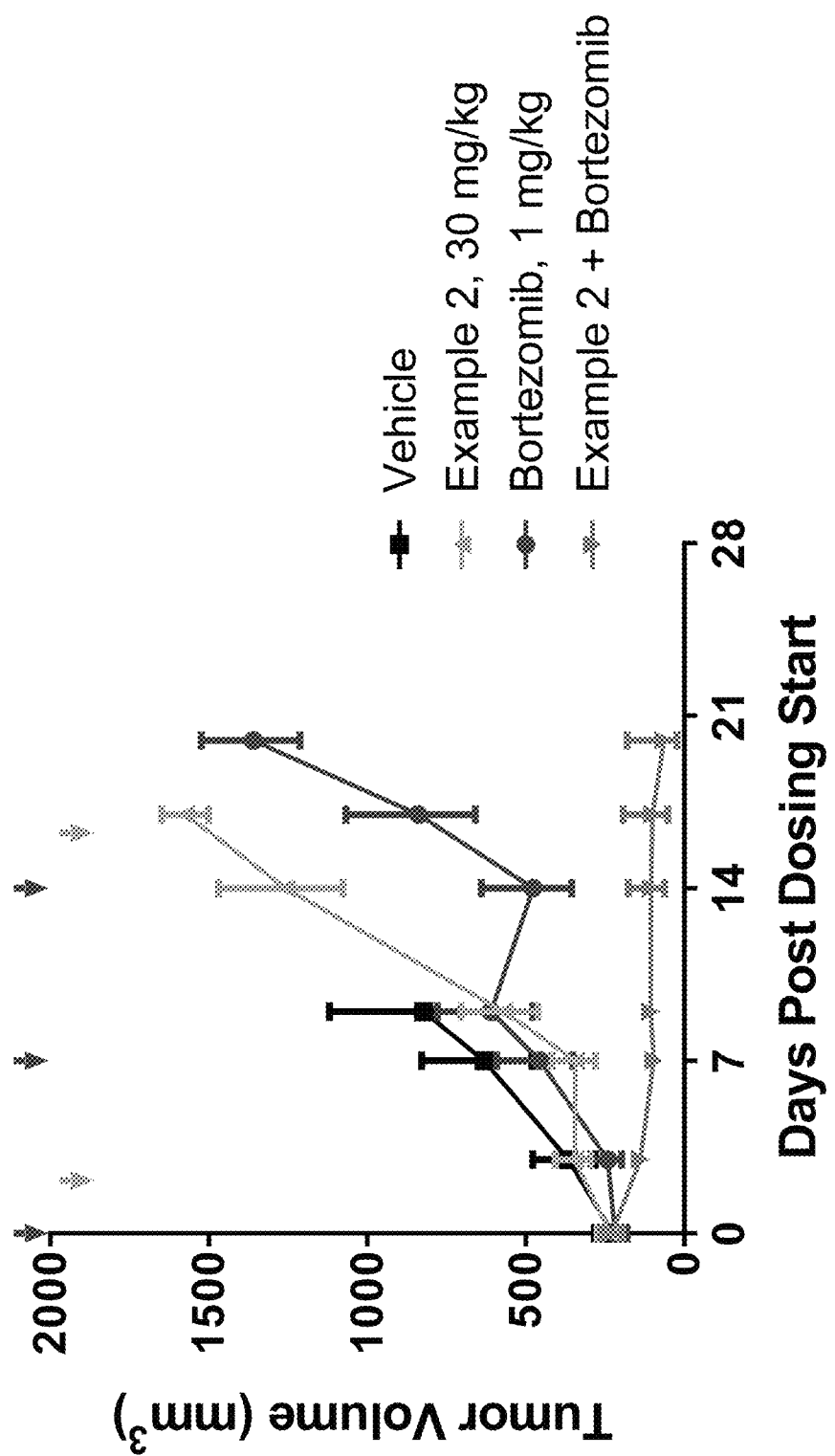
FIG. 15 illustrates the anti-tumor activity of Example 2 in combination with bortezomib in NCI-H929 tumor bearing mice.

Example 2 also demonstrated combination benefit with the proteasome inhibitor bortezomib in NCI-H929 tumor bearing mice (FIG. 15). Administration of Example 2 every other week at 30 mg/kg in combination with weekly administration of bortezomib at 1 mg/kg resulted in tumor regression whereas no significant anti-tumor activity was observed with either agent alone.

Example 7: Single Agent Activity In Vivo in a Human Acute Myeloid Leukemia Tumor Model Method:

Example 2 was formulated in 30% 2-Hydroxypropyl-beta-cyclodextrin (HPBCD), pH 9 and dosed as a single intravenous (iv) administration in a volume of 5 ml/kg. $10^6$ MV-4-11 tumor cells were injected subcutaneously in the right flank of C.B-17 SCID female mice in a volume of 0.1 mL. Tumor volumes (measured by caliper), animal body weight, and tumor conditions were recorded twice weekly for the duration of the study. Tumor volumes (measured by caliper) were calculated using the formula: length (mm)× width $(mm)^2$/0.52. For efficacy studies, mice were randomized based on tumor volumes and growth inhibition was assessed by comparison of the differences in tumor volume between control and treated groups. Dosing began when mean tumor size reached approximately 230 $mm^3$.

Figure 16:
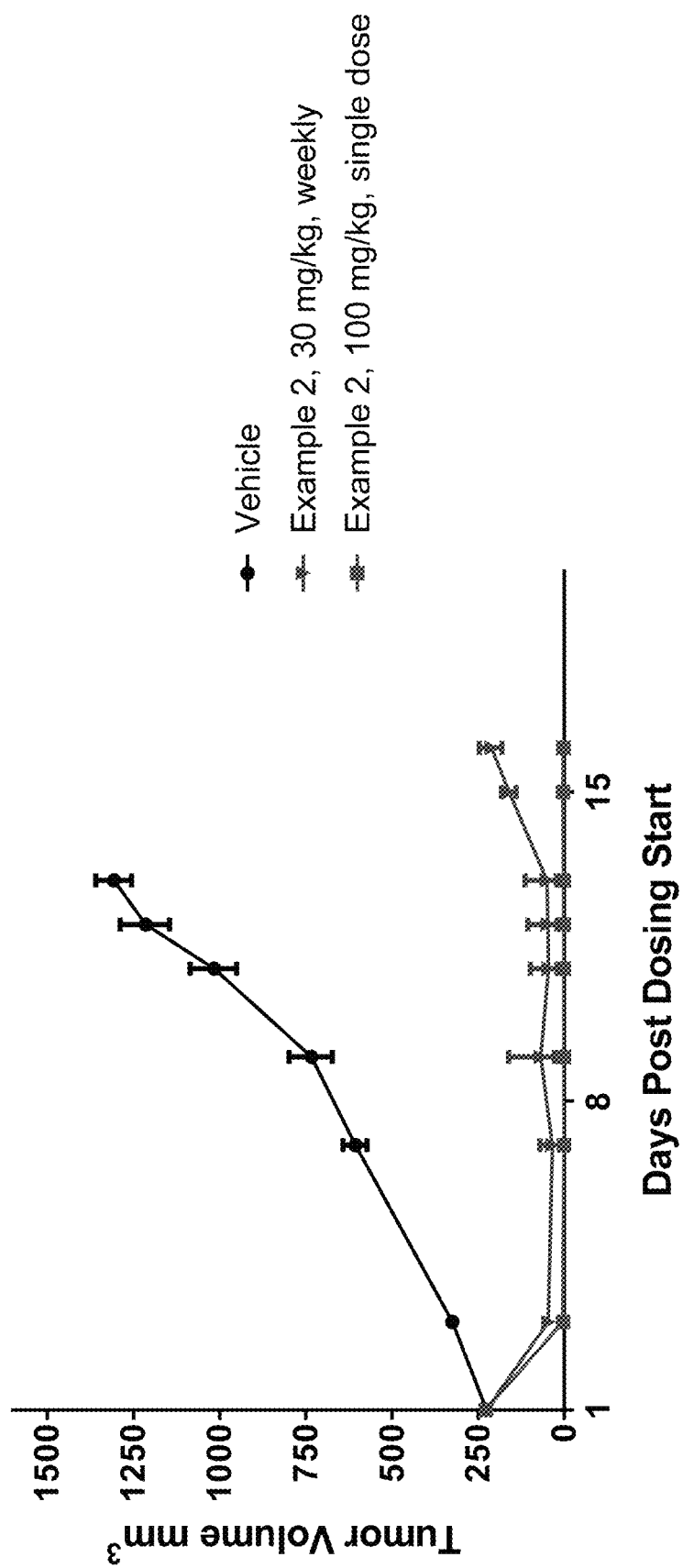
FIG. 16 illustrates tumor regression induced by Example 2 in MV-4-11 tumor bearing mice.

Results:

Treatment with Example 2 resulted in significant anti-tumor activity in mice bearing subcutaneous MV-4-11 tumors. Mice receiving a single dose of 100 mg/kg Example 2 experienced 100% tumor regression (FIG. 16). The response was durable with 4 of the 6 mice remaining tumor free 16 days after therapy. Mice receiving once weekly iv administrations of 30 mg/kg Example 2 also experienced tumor regression (~73% at Day 6) with 1 of 6 mice remaining tumor free 16 days after initiation of therapy.

Example 8: In Vitro Binding Potency of Examples 1, 2 and 3

Biochemical binding TR-FRET assay for measuring protein complex disruption TR-FRET assay was used to assess the ability of compounds to disrupt the interaction between recombinant human Mcl-1 with a labeled BIM peptide probe.

The assay was constructed such that GST tagged Mcl-1 protein, was incubated with a Europium-labeled anti-GST antibody and a HyLite Fluor 647-labeled peptide corresponding to the BH3 domain of BIM. Compound $IC_{50}$ values were assessed following a 10-point, half-$log_{10}$ dilution schema starting at 100 μM or 10 μM compound concentration. Specifically, human Mcl-1 enzyme from Mcl-1 (E171-G327) was cloned into an overexpression vector, expressed as an N-terminal GST-tagged fusion protein in *E. coli* and subsequently purified via Glutathione Sepharose-affinity and size-exclusion chromatography. The assay was performed in 384-Well LV plates (Greiner cat #784075) and run in the presence and absence of the compound of interest. Each well of 12 μL assay mixture contained 10 mM Tris (pH 7.4), 1.0 mM DTT, 0.005% Tween-20, 150 mM NaCl, 10% DMSO, and 1.5 nM GST Mcl-1, 0.5 nM LanthaScreen Eu tagged GST antibody (Invitrogen Catalog #PV5594), 4.0 nM HyLite Fluor 647-labeled BIM peptide [C(Hilyte647 C2 Maleimide)-WIAQELRRIGDEFN (SEQ ID NO:1)]. Reactions were incubated at 24° C. for 90 min before reading on a Tecan M1000 spectrfluorometer with excitation at 340 nm and emission at 612 nm & 665 nm. Subsequently, ratio of fluorescent emission intensity at 665 nm to 612 nm was calculated for each reaction, and the dose-response of the ratio to testing compound concentration was fitted to a select fit model that will provide the best fit quality using automatic parameter to derive $IC_{50}$ values for each testing compound. Table 9 provides the results from the TR-FRET Mcl1 binding assay.

Ratio Calculation=Emission 665 nm/Emission 612*10000

% inhibition=100−[(Test Ratio−Min (compound control))/(Max (DMSO control)−Min (compound control))]

TABLE 9

| Compound | Mcl-1 $IC_{50}$ (nM) |
| --- | --- |
| Example 1 (Compound I) | <3 |
| Example 2 (Compound II) | <3 |
| Example 3 (Compound III) | 67 |

Note: Caspase activity of Example 3 (Compound III) as reported in Table 1 and FRET activity of Example 3 (Compound III) as reported in Table 9 is highly dependent on enantiomeric purity since the majority of the activity arises from residual impurity of the $R_a$ enantiomer (Example 2, Compound II). As such, samples with lower enantiomeric purity exhibit increased potency in these assays. The data presented are the geometric mean of multiple measurements from samples of varying enantiomeric purity.

The invention claimed is:

1. A compound which is Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate.

2. The compound of claim 1, wherein said compound has an XRPD pattern comprising at least one peak expressed as 2θ (±0.2°) at about 7.0°.

3. The compound of claim 1, wherein said compound has an XRPD pattern comprising at least one peak expressed as 2θ (±0.2°) at about 8.4°.

4. The compound of claim 1, wherein said compound has an XRPD pattern comprising at least one peak expressed as 2θ (±0.2°) at about 12.5°.

5. The compound of claim 1, wherein said compound has an XRPD pattern comprising at least one peak expressed as 2θ (±0.2°) selected from about 7.0°, 8.4° and 12.5°.

6. The compound of claim 1, wherein said compound has an XRPD pattern comprising at least one peak expressed as 2θ (±0.2°) selected from about 5.4°, 7.0°, 8.4°, 10.7°, 12.5°, 13.1°, 14.4°, 15.1°, 15.6°, 17.1° and 18.2°.

7. The compound of claim 1, wherein the compound has a DSC thermogram comprising an endotherm with a desolvation onset at about 121° C. and a peak at about 152° C.

8. The compound of claim 1, wherein the compound has a DSC thermogram comprising an endotherm with a melting/decomposition onset at about 181° C. and a peak at about 194° C.

9. The compound of claim 1, wherein the compound has a TGA thermogram exhibiting a mass loss of about 4.0% upon heating from about 25° C. to about 160° C.

10. A pharmaceutical composition comprising a compound of claim 1 and a pharmaceutically acceptable carrier, excipient or diluent.

* * * * *